United States Patent [19]
Collins et al.

[11] Patent Number: 5,876,625
[45] Date of Patent: Mar. 2, 1999

[54] METAL LIGAND CONTAINING BLEACHING COMPOSITIONS

[75] Inventors: Terrence J. Collins; Colin P. Horwitz, both of Pittsburgh, Pa.

[73] Assignee: Carnegie Mellon University, Pittsburgh, Pa.

[21] Appl. No.: 684,670

[22] Filed: Jul. 22, 1996

[51] Int. Cl.[6] .................. C01B 15/00; C01B 15/055; C11D 3/39
[52] U.S. Cl. .................. 252/186.33; 252/186.43; 252/186.39; 510/311; 540/460; 540/465
[58] Field of Search .................. 540/460, 452, 540/465; 252/186.33, 186.43, 186.39; 510/311

[56] References Cited

U.S. PATENT DOCUMENTS 3,950,277  4/1976  Stewart et al. .................. 8/137
3,983,082  9/1976  Pratt et al. .................. 523/179

(List continued on next page.)

FOREIGN PATENT DOCUMENTS 594893  5/1994  European Pat. Off. .
717103  6/1996  European Pat. Off. .

(List continued on next page.)

OTHER PUBLICATIONS

Frank Runge, Juergen Detering, Georg Zwissler, Dieter Boeckh, Christian Schade, Binding Equilibria of Multiazo Dyes with Polymeric Dye Transfer Inhibitors, Ber. Bunsen--Ges. (1996), 100(5) , 661–670 CODEN: BBPCAX; ISSN: 0940–483X.

A. Paul Krapcho, Edwin G. E. Jahngen, Jr., and David S. Kashdan, Route to Monoesters of Malonic Acids, Tetrahedron Letters Nos. 32, pp. 2721–2723, 1994.

(List continued on next page.)

Primary Examiner—Joseph D. Anthony
Attorney, Agent, or Firm—Kirkpatrick & Lockhart LLP

[57] ABSTRACT

The invention provides a novel bleaching composition comprising:

(a) an oxidatively stable bleach activator having the structure

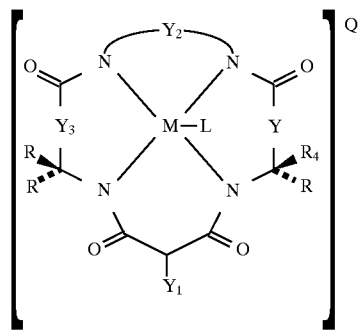

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C(R$_1$)(R$_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form notes in the Y unit, or together with a paired R substituent bound to the same carbon atom form a cycloalkyl or cycloalkenyl ring, which may include an atom other than carbon, e.g., cyclopentyl or cyclohexyl; M is a transition metal with oxidation states of I, II, III, IV, V, or VI, or selected from Groups VIA, VIIA, VIII and IB; Q is any counterion which would balance the charge of the compound on a stoichiometric basis; L is any labile ligand; and (b) an effective amount of a source of peroxy compound.

10 Claims, 4 Drawing Sheets

U.S. PATENT DOCUMENTS

| | | | |
|---|---|---|---|
| 4,119,557 | 10/1978 | Postlethwaite | 8/111 |
| 4,435,307 | 3/1984 | Barbesgaard et al. | 435/209 |
| 4,443,355 | 4/1984 | Murata et al. | 435/209 |
| 4,473,507 | 9/1984 | Bossu | 562/2 |
| 4,479,881 | 10/1984 | Tai | 510/322 |
| 4,511,490 | 4/1985 | Stanislowski et al. | 435/220 |
| 4,577,042 | 3/1986 | Collins et al. | 564/158 |
| 4,661,293 | 4/1987 | Zielske | 552/255 |
| 4,707,291 | 11/1987 | Thom et al. | 252/186.1 |
| 4,708,816 | 11/1987 | Chang et al. | 252/186.25 |
| 4,746,461 | 5/1988 | Zielske | 552/243 |
| 4,758,682 | 7/1988 | Collins et al. | 556/137 |
| 4,778,618 | 10/1988 | Fong et al. | 252/186.23 |
| 4,900,871 | 2/1990 | Ellis, Jr. et al. | 568/399 |
| 5,002,682 | 3/1991 | Bragg et al. | 252/186.26 |
| 5,182,045 | 1/1993 | Rowland et al. | 252/186.38 |
| 5,244,594 | 9/1993 | Favie et al. | 252/186.33 |
| 5,246,621 | 9/1993 | Favre et al. | 252/186.33 |
| 5,314,635 | 5/1994 | Hige et al. | 252/186.33 |
| 5,451,337 | 9/1995 | Liu et al. | 8/111 |
| 5,478,569 | 12/1995 | Berneis et al. | 424/456 |
| 5,560,748 | 10/1996 | Surutzidis et al. | 8/111 |
| 5,580,485 | 12/1996 | Ferirg et al. | 510/311 |

FOREIGN PATENT DOCUMENTS

| | | |
|---|---|---|
| 95/24267 | 9/1995 | WIPO . |
| 95/31526 | 11/1995 | WIPO . |
| 95/34628 | 12/1995 | WIPO . |
| 95/34629 | 12/1995 | WIPO . |
| 96/26831 | 9/1996 | WIPO . |

OTHER PUBLICATIONS

G. A. Fletcher and J. H. Jones, A List of Amino–Acid Derivatives Which Are Useful in Peptide Synthesis, Int. J. Peptide Protein Res. 4, 1972, 347–371, Jun. 10, 1972.

Jose M. Workman, Routes to Multimetallic High Oxidation State Transition Metal Complexes, Carnegie Mellon University, Mellon College of Science, Jul. 23, 1992.

Terrence J. Collins, Designing Ligands for Oxidizing Complexes, Department of Chemistry, Carnegie Mellon University, Accounts of Chemical Research, 1994, 27, p. 279.

Masaru Nakamura, Mitsuko Toda and Hiroko Saito, Fluorimetric Determination of Aromatuc Aldehydes With 4,5–Dimethoxyl–1, 2–Diaminobenzene, Analytica Chimica Acta, 134 (1982) 39–45.

Erich Stuart Uffelman, Macrocyclic Tetraamido–N Ligands that Stabilize High Valent Complexes of Chrominum, Maganese, Iron, Cobalt, Nickel and Copper, California Institute of Technology, Aug. 19, 1991.

Thoedora W. Greene, Protective Groups in Organic Synthesis, Harvard University, John Wiley & Sons, 1981.

Kimberely K. Kostka, Synthesis and Characterization of High–Valent Iron Complexes of Macrocyclic Tetraamido–N Ligands, Carnegie Mellon University, Jul. 19, 1993.

Nathan L. Drake, Harry D. Anspon, et al., Synthetic Antimarlarials. Some Derivatives of 8–Aminoquinoline, Laboratories of the University of Maryland, vol. 68, p. 1536, Aug. 1946.

Richard J. Bushby and Michael D. Pollard, The Introduction of Alkylidene Substituents into the 4–Position of the 3,3,5, 5,–Tetramethyl—pyrazoline Nucleus by the Thioketone plus Diazoalkane Reaction: Synthesis of Tetrasubstituted Episulphides and Alkenes, (1979).

Kimberly L. Kostka, Brian G. Fox, et al., High Valent Transition Metal Chemistry. Mossbauer and EPR Studies of High–Spin (S=2) Iron (IV) and Intermediate–Spin (S =3/2) Iron (III) Complexes with a Macrocyclic Tetraamido–N Ligand Date Considered (Jan. 4, 1993).

Mohammad Shakir and Saji P. Varkey, A New Synthetic Route for the Preparation of a New Series of 14–22–Membered Tetraoxomacrocyclic Tetraamines and Their Transition Metal Complexes, (Jul. 1994).

Lemin et al., The Dyeing of Direct Dyes on Cotton, The Journal of the Society of Dyers & Colourists, Vol. LXII, (1946.).

Thomas Vickerstaff, The Physical Chemistry of Dyeing, Imperial Chemical Industries Limited, (1954).

Catalyst:
0.4 mM [Fe(H₂O)DCB*]⁻
0.4 mM [Fe(H₂O)DCB]⁻
0.0 mM catalyst
12 μM pinacyanol chloride dye
4 mM 30% H₂O₂ oxidant
pH ~ 9 NaHCO₃/Na₂CO₃

* = dye addition

METAL LIGAND CONTAINING BLEACHING COMPOSITIONS

BACKGROUND OF THE INVENTION

1. Field of the Invention

The invention relates to the use of macrocyclic metal ligand complexes as bleaching catalysts, and more particularly, to transition metal complexes of macrocyclic tetraamide ligands as catalysts for enhancing oxidative bleaching reactions.

2. Brief Statement on Related Art

Hydrogen peroxide, and other peroxy compounds which yield hydrogen peroxide in aqueous solution, have long been known for use in fabric and surface bleaching. However, peroxy compounds, such as sodium perborate (monohydrate or tetrahydrate), sodium percarbonate, and the like, have relatively mild bleaching performance at low temperatures (e.g., below 100° C./38.8° F.). Organic peroxyacids, such as perbenzoic acid, are stronger oxidants, but are often unstable unless stabilized by costly and cumbersome methods. In addition, the premade peroxyacids are often cost-ineffective to manufacture. Bleach activators, or peracid precursors, such as esters, ketones, nitrites, or the like, are often effective at enhancing the efficacy of peroxy compounds. However, the bleach activators must usually be present in stoichiometric or greater quantities and can also be costly to manufacture.

Transition metal chelates, especially those using manganese and iron, are known as bleaching catalysts for peroxy compounds. These are represented by, for example, Favre et al., U.S. Pat. No. 5,246,621, Bragg et al., U.S. Pat. No. 5,002,682, Postlethwaite, U.S. Pat. No. 4,119,557, and Ellis, Jr et al., U.S. Pat. No. 4,900,871. These transition metal chelates can be used, for example, in laundering fabrics with an appropriate peroxy compound, for example, sodium perborate monohydrate.

While these transition metal chelates have been proven to improve the oxidizing power of peroxy compounds, they sometimes can mediate dye and, even damage, to fabrics when used as bleaching activators.

Certain transition metal chelates have been researched for unrelated purposes. For example, complexes of high oxidation state transition metals are known to function as oxidants in numerous biological reactions under the influence of a protein matrix and in recent years a widespread interest in understanding the mechanism of action and the reactivity of certain monooxygenase catalysts has developed.

An exemplary program is described in Collins, T. J., "Designing Ligands for Oxidizing Complexes," *Accounts of Chemical Research*, 279, Vol. 27, No. 9 (1994). This article lays out a design oriented approach for obtaining ligands that are resistant to oxidative degradation when coordinated to highly oxidizing metal centers. Several diamido-N-diphenoxido and diamido-N-alkoxido acyclic chelate compounds and macrocyclic tetraamido-N chelate compounds are described in the Collins *Accounts of Chemical Research* article.

An azide based synthetic route to macrocyclic tetraamido ligands is described in Uffelman, E. S., Ph.D. Thesis, California Institute of Technology, (1992). Additionally, synthesis of an aryl bridged tetraamido ligand via the azide based route can proceed by using an aromatic diamine as a starting material.

However, the art has not recognized that certain macrocyclic tetraamido ligands will provide novel and unusually effective bleach activators for peroxy compounds. Additionally, it has not been taught, disclosed or suggested that these types of compounds will be unusually advantageous in the areas of dye transfer inhibition, anti-soil redeposition and stain removal.

SUMMARY OF THE INVENTION

The invention comprises a bleaching composition comprising:

(a) an oxidatively stable bleach activator having the structure

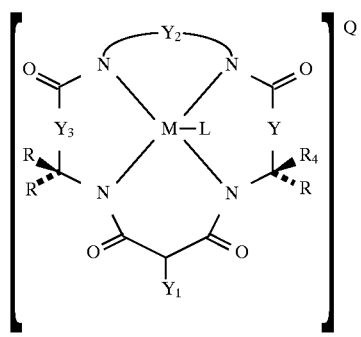

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C(R$_1$)(R$_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form notes in the Y unit, or together with a paired R substituent bound to the same carbon atom form a cycloalkyl ring, which may include an atom other than carbon, e.g., cyclopentyl or a cyclohexyl ring; M is a transition metal with oxidation states of I, II, III, IV, V, or VI, or selected from Groups 6, 7, 8, 9, 10 and 11 of the Periodic Table; Q is any counterion which would balance the charge of the compound on a stoichiometric basis; L is any labile ligand; and (b) an effective amount of a source of peroxy compound.

Surfactants, fillers, builders, sequestrants, anti-oxidants, enzymes, fluorescent whitening agents, dyes, colorants, pigments, and other standard cleaning and/or laundering adjuncts may be added.

The preferred bleach activators are macrocyclic tetraamido compounds. Of these, those having a substituted aromatic substituent fused directly into the ligand's cyclic structure are especially preferred.

For example, a preferred compound has the structure:

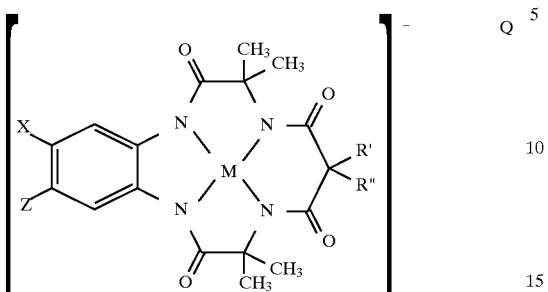

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon; M is a transition metal with oxidation states of I, II, III, IV, V, or VI, or selected from Groups 6, 7, 8, 9, 10 and 11 of the Periodic Table; Q is any counterion which would balance the charge of the compound on a stoichiometric basis.

It is therefore an object of this invention to provide a macrocyclic tetraamido compound as a peroxy bleach activator.

It is another object of this invention to provide a novel bleach activator which has improved dye transfer inhibition.

It is still another object of this invention to provide a novel bleach activator which has improved anti-soil redeposition properties.

It is yet another object of this invention to provide a novel bleach activator which has unique stain removal performance.

It is a further object of this invention to provide a novel bleach activator which has sustained catalytic stability in a buffered solution.

It is still a further object of this invention to provide a novel bleach activator which can be used in substoichiometric amounts relative to the peroxy compound.

DETAILED DESCRIPTION OF THE PREFERRED EMBODIMENTS

Figure 1:
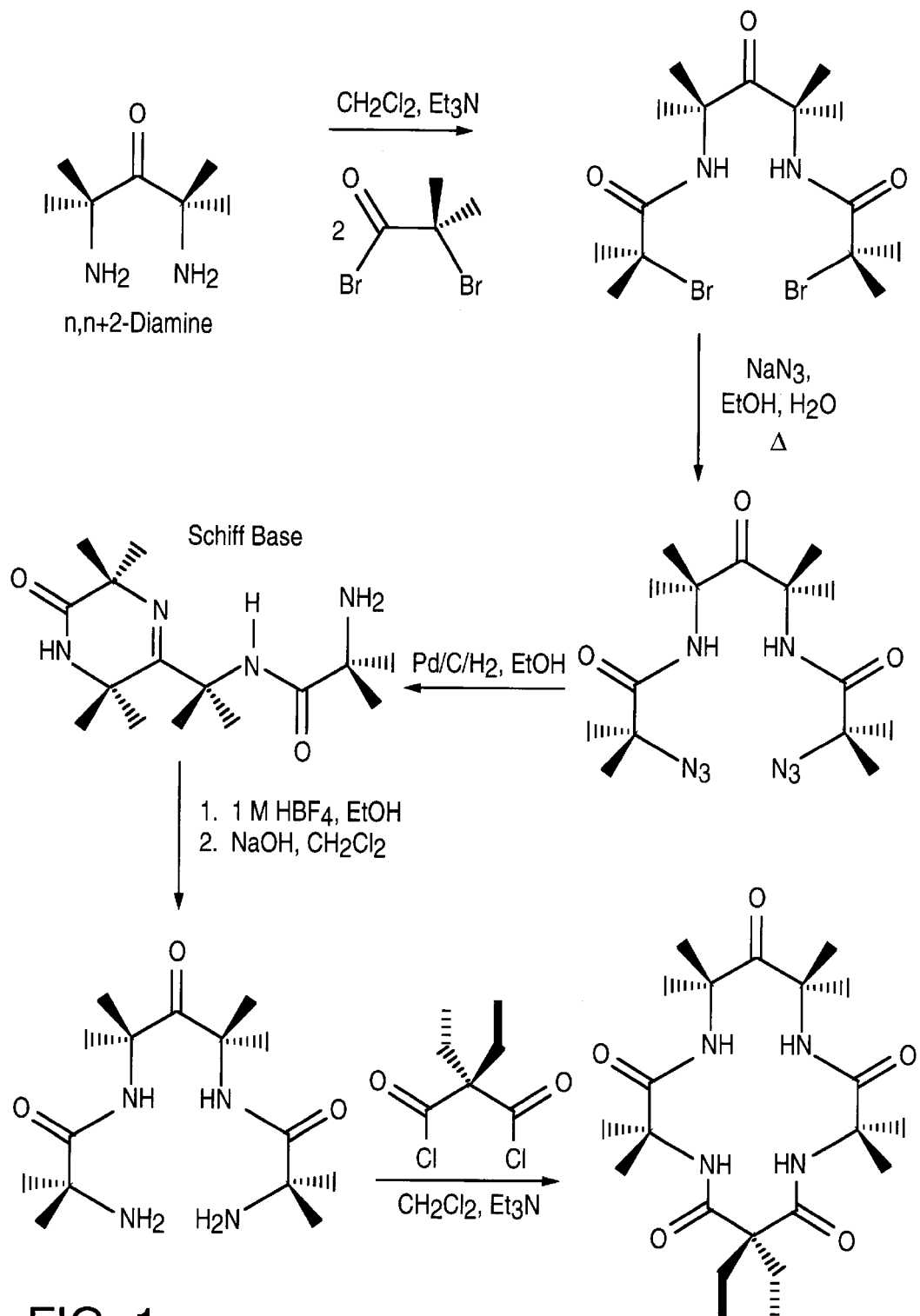
FIG. 1 depicts a synthetic route for preparing the macrocyclic tetraamido ligands of the invention via the azide route.
Figure 2:
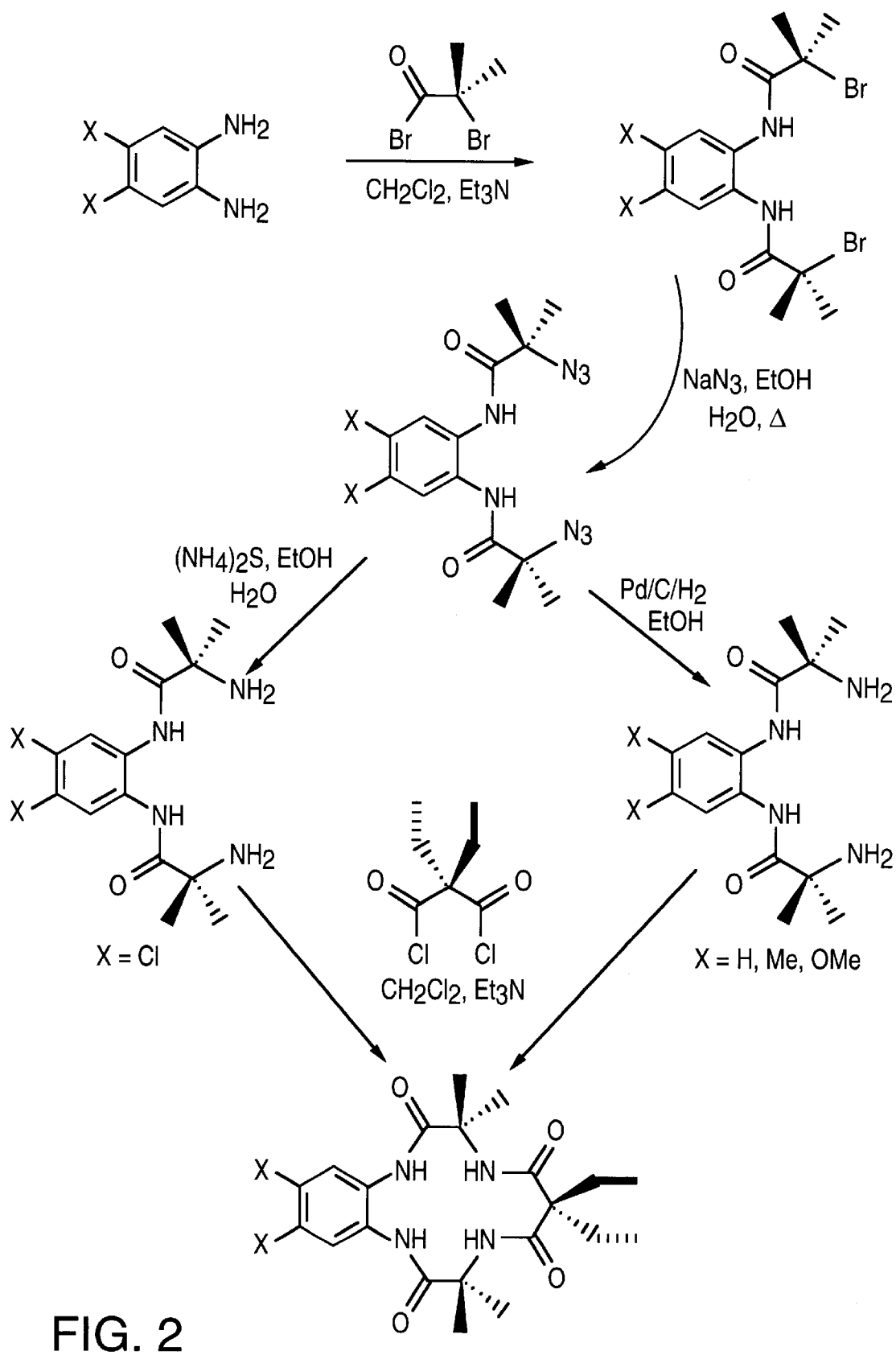
FIG. 2 depicts a synthetic route for preparing the macrocyclic tetraamido ligands of the invention via the azide route using an aromatic diamine as a starting material.

The invention comprises a bleaching composition comprising:

(a) an oxidatively stable bleach activator having the structure

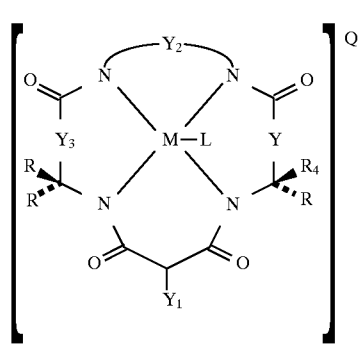

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C($R_1$)($R_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form notes in the Y unit, or together with a paired R substituent bound to the same carbon atom form a cycloalkyl or cycloalkenyl ring, which may include an atom other than carbon, e.g., cyclopentyl or a cyclohexyl ring; M is a transition metal with oxidation states of I, II, III, IV, V, or VI, or selected from Groups 6, 7, 8, 9, 10 and 11 of the Periodic Table; Q is any counterion which would balance the charge of the compound on a stoichiometric basis; L is any labile ligand; and (b) an effective amount of a source of peroxy compound.

Of these, the preferred inventive macrocyclic tetraamido ligands have proven to be surprisingly effective in a diverse group of performance characteristics for bleach activators.

These ligands are prepared in accordance with the procedures set forth in the concurrently filed and co-pending patent applications of Gordon-Wylie et al., entitled SYNTHESIS OF MACROCYCLIC TETRAAMIDO-N LIGANDS, Ser. No. 08/681,187 filed on even date herewith, now abandoned and of Collins et al., entitled LONG-LIVED HOMOGENOUS OXIDATION CATALYSTS, Ser. No. 08/681,237 filed on even date herewith, now abandoned both of which are incorporated herein by reference.

1. The Macrocyclic Tetraamido Ligands

The inventive compounds have the structure:

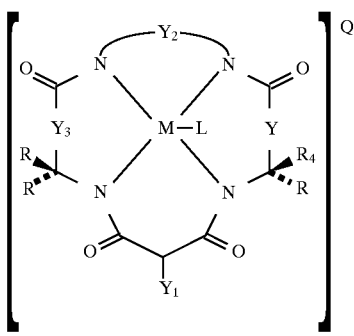

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C($R_1$)($R_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form notes in the Y unit, or together with a paired R substituent bound to the same carbon atom form a cycloalkyl or cycloalkenyl ring, which may include an atom other than carbon, e.g., cyclopentyl or a cyclohexyl ring; M is a transition metal with oxidation states of I, II, III, IV, V, or VI, or selected from Groups 6, 7, 8, 9, 10 and 11 of the Periodic Table; Q is any counterion which would balance the charge of the compound on a stoichiometric basis; L is any labile ligand.

An especially preferred embodiment of these inventive compounds is represented by the structure of the macrocyclic tetraamido compounds:

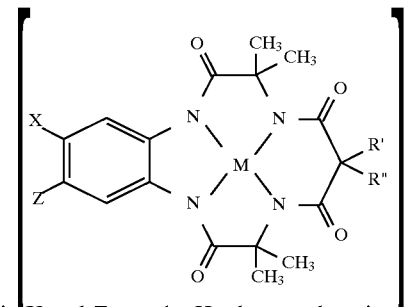

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon; M is a transition metal with oxidation states of I, II, III, IV, V, or VI, or selected from Groups 6, 7, 8, 9, 10 and 11 of the Periodic Table; and, Q is any counterion which would balance the charge of the compound on a stoichiometric basis.

The X and Z groups can be H, or either electron donors or electron withdrawing groups. Electron withdrawing groups include halogens, such as Br, I and most preferably, Cl$^-$. Further, $SO_3^-$, $OSO_3^-$, $OSO_3$ R (R being defined, without limitation, as H, alkyl, aryl, alkylaryl) and $NO_2^-$ are appropriate groups. Electron donor groups include alkoxy (without limitation, methoxy, ethoxy, propoxy and butoxy), alkyl (without limitation, methyl, ethyl, propyl, n-butyl and t-butyl) and hydrogen. These groups change the electron density of the metal ligand complex and impact its reactivity.

R' and R" appear to have an impact on the sustained catalytic stability of the inventive macrocylic tetraamido ligands. Although each can be individually chosen from H, alkyl, alkenyl, aryl, alkynyl, halogen, alkoxy, or phenoxy substituents, short chain alkyl appears preferred. Especially preferred is when R' and R" are the same and are selected from ethyl and methyl, or when R' and R" combine to form a cycloalkyl or cycloalkenyl ring, especially cyclopentyl or cyclohexyl. The cycloalkyl ring may include at least one other atom other than carbon, such as, without limitation, N, O, or S.

The compounds of the present invention form robust, long-lived oxidation catalysts and precatalysts. For the sake of convenience, and without limiting the scope of the invention, "catalyst" will be used herein to include precatalysts and actual catalyst complexes, where the latter is the species that carries out the oxidation. In many cases, the precise catalytic mechanism is not known and thus the precise role in any given oxidation reaction of the chelate system of the present invention may not be known. As used herein, robust oxidation catalyst means that when the catalyst is added to a solvent in the presence of an oxidant, such as a peroxide, the half-life of the activated form of the metal complex is 30 seconds or more. The half-life is the time in which half of the metal complex decomposes or degrades.

Surprisingly, the design of one of the most preferred embodiments of the new robust compounds differs from the prior art compounds by only one constituent. By changing the R', R" diethyl substituents of the prior art tetraamido compounds to dimethyl substituents, the previously fragile, short-lived chelate complexes are transformed unexpectedly into stable, long-lived complexes which are very resistant to oxidative degradation. What appeared to be a minor change in the structure is in fact the key to a new class of robust long-lived oxidation catalysts. The C—H bond strength of the methyl substituent is about 3 Kcal.mol$^{-1}$, greater than the C—H bond strength of the corresponding ethyl substituent. It has been determined that any R', R" substituents which are unreactive, or which form strong bonds with the cyclic carbon, or are sterically or conformational hindered, such that they are restricted from intramolecular reaction with the axial oxo ligand will also form the robust catalysts, or precatalysts of the invention.

The importance of the bond strength and/or conformational constraints can be seen from the following determinations.

Figure 4:
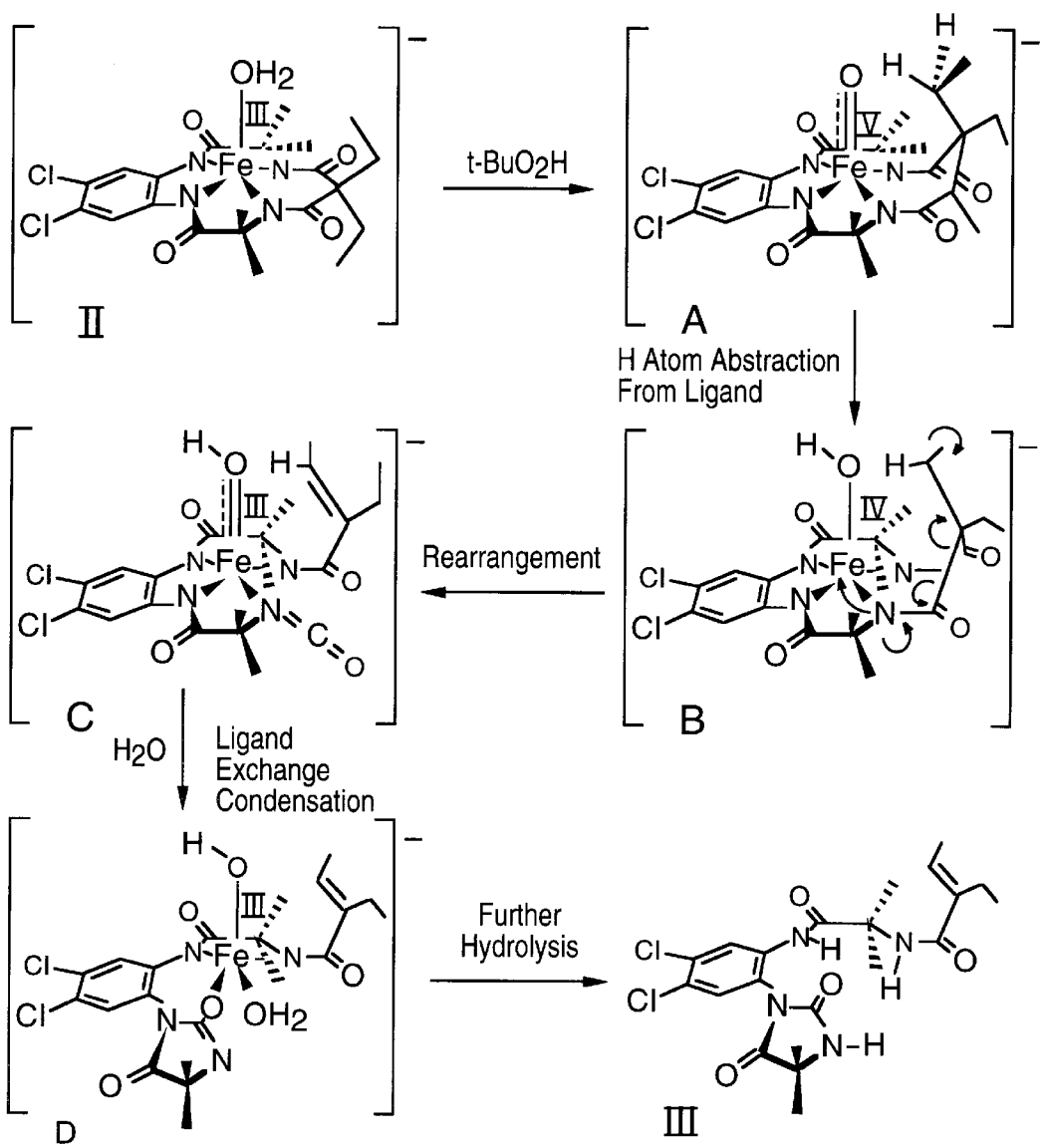

In order to support oxidation catalysis, every component of the ligand system must be substantially resistant to oxidative degradation. The key to the stability of the R' and R" groups has been determined by observation in a particularly informative case. As shown in FIG. 4, iron (III) aqua complexes react with hydroperoxides to give a purported oxo complex which it has been shown exhibit catalytic properties for the oxidation of nitrites containing C—H bounds a to the cyano group. However, as catalysis proceeds the ligand system slowly decomposes and it is proposed that this degradation proceeds via abstraction of an H-atom from a methylene group of an ethyl substituent in the R' and R" position as is consistent with the structure of the hydantoin-ring containing degradation product, labeled III (FIG. 4). Molecular models reveal that a highly strained conformation of the Y-containing chelate ring is required to bring the abstractable H-atom close to the abstracting O-atom. Compound III has been unambiguously characterized by a variety of mass spectrometric, $^1$H and $^{13}$C NMR, K elemental analyses. Simultaneously with the observed degradation, the system catalytically oxidizes the weakest C—H bond in a series of nitriles [(CH$_3$)$_2$CHCN, CH$_3$CH$_2$CN, CH$_3$CN, CD$_3$CN] which are employed as solvents. The products are mixtures of nitrile oxidation products. Thus, where t-butyl hydroperoxide is the primary oxidant, the product mixture with (CH$_3$)$_2$CHCN as the substrate contains (CH$_3$)$_2$C(OH)CN, (CH$_3$)$_2$(CN)COOC(CH$_3$)$_3$, (CH$_3$)$_2$(CN)COOCH$_3$, (CH$_3$)$_2$C=O, (CH$_3$)$_3$COH. It has also been shown that while this product mixture suggests a free radical autoxidation process where the role of the iron complex, II (FIG. 4), would be to initiate the process, free radical autoxidation cannot be the dominant mechanism. Thus, when the oxidation is carried out under $^{18}$O$_2$ (1 atm,>98%) the yield of $^{18}$O$_2$ labelled products is too low for the reaction mechanism to be consistent with a completely free radical autoxidation process. By replacement of CH$_3$— for CH$_3$CH$_2$— in the R' and R" position, the ligand degradation is dramatically suppressed such that nitrile oxidation alone dominates the oxidative reactivity. This inhibition of ligand degradation by the CH$_3$— for CH$_3$CH$_2$— can be rationalized as resulting from the increased C—H bond strength of CH$_3$— versus CH$_3$CH$_2$—, ca.$^3$ kcal/mol$^{-1}$, thereby slowing the rate of the H-atom abstraction by the oxo ligand by ca. three orders of magnitude. Since it is apparent that the abstraction is critical to the degradation, the orientation of the abstractable H-atom with respect to the oxo ligand is also critical as this orientation determines the distance of approach and abstraction reactions are exquisitely distance dependent. Molecular models reveal that if a cyclopentyl unit is employed to replace the ethyl groups of R' and R", the methylenic C—H group equivalent to that abstracted from the ethyl C—H group cannot reach the oxo ligand without considerably more ring-strain than that found in the ethyl case. Thus, the conformational constraint approach serves to dramatically increase the resistance of a so-substituted chelate to oxidative degradation.

Figure 5:
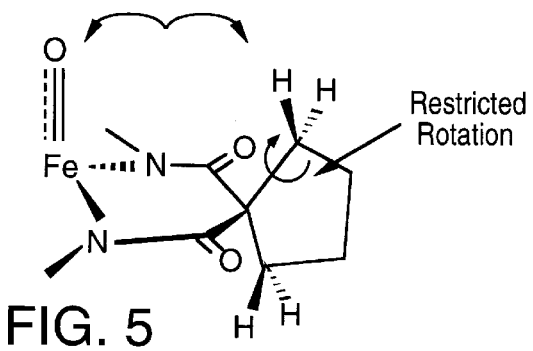

In the structure shown in FIG. 5, the oxo group and methylenic H are restricted from as close an approach as in the ethyl case because the methylene group of the cyclopentyl substituent cannot rotate freely to bring the two groups into as close a juxaposition.

The compounds of the present invention are macrocyclic, comprised of four anionic donor ligands which result in concert to form a substantially planar tetradentate platform which can be complexed with a metal and axial ligand to form the chelate/catalyst system of the present invention. The preferred design for producing robust ligands is a macrocyclic tetraamido ligand having no hydrogens α to N-amido donor groups. When coordinated with the metal ion, five- and six-membered chelate rings are most stable. The substituents can vary considerably provided they meet the requirements described above. This is particularly critical for the R' and R" substituents.

The tetradentate macrocyclic compound of the present invention is designed to be complexed with a metal, preferably a transition metal.

The metal M is a transition metal with oxidation states of I, II, III, IV, V, or VI; or preferably selected from Groups 6,7 8, 9, 10, 11 and 12 of the Periodic Table. It is preferably selected from the group consisting of Fe, Mn, Cr, Cu, Co, Ni, Mo, Zn, and W. Mixtures thereof may be possible.

Q is any counterion which would balance the charge of the compound (generally, negative; preferably −1) on a stoichiometric basis. Thus, the generally postitively charged counterion is preferably chosen, but not limited to: alkali metal counterions (e.g., K, Li, Na), NR$^*_4$ and PR$^*_4$, wherein each R$^*$ is individually selected from H, alkyl, aryl, alkylaryl, alkenyl, or can fuse together to form a cycloalkyl or cycloalkenyl or aryl ring which may contain at least one atom other than carbon.

L is any labile ligand which can attach to M. These include, preferably, but without limitation, H$_2$O, Cl, and C≡N.

In the preferred embodiment, the axial ligand, L, is labile because it occupies its position relative to the metal until the chelate system is introduced into a solution containing an oxidant. The label ligand will dissociate in solution and will be replaced by the oxidant, most generally an O-atom transfer agent, but also any general oxidant that can serve to activate the metal ion to perform catalysis.

Because of the complex nature of these compounds, within the specification, they are not named, but for convenience are referred to by the substituents present in them. The structure represented above, for example, can be titled 5,6:(4,5-Di-X-Benzo)-3,8,11,13 -tetraoxo-2,2,9,9-tetramethyl- 12,12-diethyl- 1,4,7,10-tetra azacyclotridecane (or Tetramethyl diethyl di-X-benzene (TMDE-DXB, where X=Cl, H, Me, OMe)). Thus, for convenience, in the above structure, where there are two methyl groups each on the amine members of the ligand, and there are two ethyl groups acting as R' and R", the compound is referred to as TMDE. When the groups X and Z are both chloro, the compound is referred to as DCB. The preferred transition metal of the ligand is iron, so the compound can be referred to as FeDCB.

As the inventive macrocyclic tetraamido ligands are true catalysts, the amount thereof added to the bleaching compositions is generally substoichiometric. However, it is preferred, without limitation, to add about 0.0001—about 999,999 parts per million (ppm), more preferably 0.001–100,000 ppm, to the compositions of the invention.

In the Experimental Section below, selected syntheses of the preferred macrocyclic tetraamido compounds are depicted. Additionally, tests were conducted to demonstrate the dye transfer inhibition properties, the sustained catalytic activity and the stain removal performance of these inventive macrocyclic ligands.

2. Peroxy Compounds

The peroxy compound can be an organic or inorganic compound containing the —O—O— peroxide linkage. Exemplary compounds include hydrogen peroxide, hydrogen peroxide adducts, compounds capable of producing hydrogen peroxide in aqueous solution, organic peroxides, persulfates, perphosphates, and persilicates. Hydrogen peroxide adducts include alkali metal (e.g., sodium, lithium, potassium) carbonate peroxyhydrate and urea peroxide. Compounds capable of producing hydrogen peroxide in aqueous solution include alkali metal (sodium, potassium, lithium) perborate (mono- and tetrahydrate). The perborates are commercially available from such sources as Akzo N. V., and FMC Corporation. Alternatively, an alcohol oxidase enzyme and its appropriate alcohol substrate can be used as a hydrogen peroxide source. Organic peroxides include, without limitation, benzoyl and cumene hydroperoxides. Persulfates include potassium peroxymonosulfate (sold as Oxone®, E. I. du Pont de Nemours) and Caro's acid.

An effective amount of peroxy compound is an amount sufficient to generate at least 0.001 ppm active oxygen (A.O.). While not limited thereto, it is preferred to produce from about 0.001 to about 1,000 ppm A.O. For fabric bleaching, from about 0.01 to about 50 ppm A.O. is preferred. A description of, and explanation of, A.O. measurement is found in the article of Sheldon N. Lewis, "Peracid and Peroxide Oxidations," In: *Oxidation*, 1969, pp. 213–258, which is incorporated herein by reference.

3. Cleaning and/or Laundering Adjuncts

The inventive macrocyclic tetraamido ligands can be combined with an oxidant bleach or detergent base, said base comprising: builders; and optionally, a surfactant selected from the group consisting of anionic, nonionic, cationic, amphoteric, zwitterionic surfactants, and mixtures thereof. Other adjunct materials may be present. These compounds can also be presented in a liquid base, for a hard surface, stain remover, or other surface cleaning/bleaching execution. These compounds may also be useful for pulp and textile bleaching processing. Each of these components, and adjunct materials suitable for use herein are further discussed below:

a. Builders

The builders are typically alkaline builders, i.e., those which in aqueous solution will attain a pH of 7–14, preferably 9–12. Examples of inorganic builders include the alkali metal and ammonium carbonates (including sesquicarbonates and bicarbonates), phosphates (including orthophosphates, tripolyphosphates and tetrapyrophosphates), aluminosilicates (both natural and synthetic zeolites), and mixtures thereof. Carbonates are especially desirable for use in this invention because of their high alkalinity and effectiveness in removing hardness ions which may be present in hard water, as well as their low cost. Carbonates can be used as the predominant builder. Silicates ($Na_2O:SiO_2$, modulus of 4:1 to 1:1, most preferably about 3:1 to 1:1) can also be used. Silicates, because of their solubility in water and ability to form a glassy matrix, can also be advantageously used as a binder for the detergent.

Organic builders are also suitable for use, and are selected from the group consisting of the alkali metal and ammonium sulfosuccinates, polyacrylates, polymaleates, copolymers of acrylic acid and maleic acid or maleic anhydride, citrates and mixtures thereof.

b. Fillers/Diluents

Fillers for the bleach composition or detergent are used to ensure the correct amount or dose of washing or cleaning actives is delivered per wash or cleaning usage. Salts such as NaCl, $Na_2SO_4$, and borax, are preferred. Organic diluents, such as sugar, are possible. If in a liquid execution, solvents (such as, without limitation, alkanols, gycols, glycol ethers, hydrocarbons, ketones, and carboxylic acids), liquid surfactants and water could be used as diluents.

c. Surfactants

Surfactants will generally be added to bleach or detergent formulations for removal of particular targeted soils, e.gs., nonionic surfactants on oily soils, and anionic surfactants on particulate soils. However, generally speaking, oxidant bleach compositions may contain little or even no surfactant.

Particularly effective surfactants appear to be anionic surfactants. Examples of such anionic surfactants may include the ammonium, substituted ammonium (e.g., mono-, di-, and tri- ethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarcosinates and acyl N-methyltaurides. Preferred are alkylaryl sulfonated surfactants, such as alkylbenzene sulfonates.

Other preferred surfactants of use include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers of propylene oxide and ethylene oxide with propoxylated ethylene diamine. Also included are such semi-polar nonionic surfactants like amine oxides, phosphine oxides, sulfoxides, and their ethoxylated derivatives.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear substituents such as phenyl groups.

Further, suitable amphoteric and zwitterionic surfactants which contain an anionic water-solubilizing group, a cationic group and a hydrophobic organic group may include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds. Other examples of potentially suitable zwitterionic surfactants can be found described in Jones, U.S. Pat. No. 4,005,029, at columns 11–15, which are incorporated herein by reference.

Further examples of anionic, nonionic, cationic and amphoteric surfactants which may be suitable for use in this invention are depicted in Kirk-Othmer, *Encyclopedia of Chemical Technology*, Third Edition, Volume 22, pages 347–387, and *McCutcheon's Detergents and Emulsifiers*, North American Edition, 1983, which are incorporated herein by reference.

As mentioned hereinabove, other common detergent adjuncts may be added if a bleach or detergent bleach product is desired. If, for example, a detergent composition is desired, the following ranges (weight %) appear practicable:

| | |
|---|---|
| 0.5–50.0% | Hydrogen Peroxide Source |
| 0.0001–10,000 ppm | Activator |
| 1.0–50.0% | Surfactant |
| 1.0–50.0% | Builder |
| 5.0–99.9% | Filler, stabilizers, dyes, fragrances, brighteners, etc. | d. Chelating Agents

In some of the compositions herein, it is especially preferred to include a chelating agent, most preferably, an aminopolyphosphonate. These chelating agents assist in maintaining the solution stability of the oxidant in order to achieve optimum performance. In this manner, they are acting to chelate free heavy metal ions. The chelating agent is selected from a number of known agents which are effective at chelating free heavy metal ions. The chelating agent should be resistant to hydrolysis and rapid oxidation by oxidants. Preferably, it should have an acid dissociation constant ($pK_a$) of about 1–9, indicating that it dissociates at low pH's to enhance binding to metal cations. The most preferred chelating agent is an aminopolyphosphonate which is commercially available under the trademark Dequest, from Monsanto Company. Examples thereof are Dequest 2000, 2041, 2060 and 2066. (See also Bossu, U.S. Pat. No. 4,473,507, column 12, line 63 through column 13, line 22, incorporated herein by reference). A polyphosphonate, such as Dequest 2010, is also suitable for use. Other chelating agents, such as ethylenediaminetetraacetic acid (EDTA) and nitrilotriacetic acid (NTA) may also be suitable for use. Still other new, preferred chelating agents are new propylenediaminetetraacetates, such as Hampshire 1,3 PDTA, from W. R. Grace, and Chel DTPA 100#F, from Ciba-Geigy A. G. Mixtures of the foregoing may be suitable. Effective amounts of the chelating agent range from 1–1,000, more preferably 5–500, most preferably 10–100 ppm chelating agent, in the wash liquor.

e. Other Adjuncts:

The standard detergent or oxidant bleach adjuncts can be included in the present invention.

These include enzymes are especially desirable adjunct materials in these detergent or oxidant bleach products. However, it may be preferred to include an enzyme stabilizer.

Proteases are one especially preferred class of enzymes. They are selected from acidic, neutral and alkaline proteases. The terms "acidic," "neutral," and "alkaline," refer to the pH at which the enzymes' activity are optimal. Examples of neutral proteases include Milezyme (available from Miles Laboratory) and trypsin, a naturally occurring protease. Alkaline proteases are available from a wide variety of sources, and are typically produced from various microorganisms (e.g., *Bacillis subtilisis*). Typical examples of alkaline proteases include Maxatase and Maxacal from International BioSynthetics, Alcalase, Savinase and Esperase, all available from Novo Industri A/S. See also Stanislowski et al., U.S. Pat. No. 4,511,490, incorporated herein by reference.

Further suitable enzymes are amylases, which are carbohydrate- hydrolyzing enzymes. It is also preferred to include mixtures of amylases and proteases. Suitable amylases include Rapidase, from Societe Rapidase, Milezyme from Miles Laboratory, and Maxamyl from International BioSynthetics.

Still other suitable enzymes are cellulases, such as those described in Tai, U.S. Pat. No. 4,479,881, Murata et al., U.S. Pat. No. 4,443,355, Barbesgaard et al., U.S. Pat. No. 4,435,307, and Ohya et al., U.S. Pat. No. 3,983,082, incorporated herein by reference.

Yet other suitable enzymes are lipases, such as those described in Silver, U.S. Pat. No. 3,950,277, and Thom et al., U.S. Pat. No. 4,707,291, incorporated herein by reference.

Still further enzymes of interest herein are peroxidases, such as horseradish peroxidase, and those disclosed in WO 93/24628, incorporated herein by reference.

The enzyme may be present in an amount of about 0–5%, more preferably about 0.01–3%, and most preferably about 0.1–2% by weight of the detergent/bleach/cleaner base.

Mixtures of any of the foregoing hydrolases are desirable, especially protease/amylase blends.

Additionally, optional adjuncts include dyes, such as Monastral blue and anthraquinone dyes (such as those described in Zielske, U.S. Pat. No. 4,661,293, and U.S. Pat. No. 4,746,461).

Pigments, which are also suitable colorants, can be selected, without limitation, from titanium dioxide, ultramarine blue (see also, Chang et al., U.S. Pat. No. 4,708,816), and colored aluminosilicates.

Fluorescent whitening agents are still other desirable adjuncts. These include the stilbene, styrene, and naphthalene derivatives, which upon being impinged by ultraviolet light, emit or fluoresce light in the visible wavelength. These FWA's or brighteners are useful for improving the appearance of fabrics which have become dingy through repeated soilings and washings. Preferred FWA's are Tinopal 5BMX-C and Tinopal RBS, both from Ciba Geigy A. G., and Phorwite RKH, from Mobay Chemicals. Examples of suitable FWA's can be found in U.S. Pat. Nos. 1,298,577, 2,076,011, 2,026,054, 2,026,566, 1,393,042; and U.S. Pat. Nos. 3,951,960, 4,298,290, 3,993,659, 3,980,713 and 3,627,758, incorporated herein by reference.

Anti-redeposition agents, such as carboxymethylcellulose, are potentially desirable. Next, foam boosters, such as appropriate anionic surfactants, may be appropriate for inclusion herein. Also, in the case of excess foaming resulting from the use of certain surfactants, anti-foaming agents, such as alkylated polysiloxanes, e.g., dimethylpolysiloxane, would be desirable. Fragrances are also desirable adjuncts in these compositions.

Additional organic bleach activators can be added, including, but not limited to, esters (see Fong et al., U.S. Pat. No. 4,778,618 and Rowland et al., U.S. Pat. No. 5,182,045), ketones, imides (See Kaaret, U.S. Pat. No. 5,478,569) and nitrites.

The additives may be present in amounts ranging from 0–50%, more preferably 0–30%, and most preferably 0–10%. In certain cases, some of the individual adjuncts may overlap in other categories. However, the present invention contemplates each of the adjuncts as providing discrete performance benefits in their various categories.

EXPERIMENTAL SECTION

Syntheses of Oxidatively Robust Tetraamido Ligands

Materials. All solvents and reagents were reagent grade (Aldrich, Aldrich Sure-Seal, Fisher) and were used as received. Microanalyses were performed by Midwest Microlabs, Indianapolis, Ind.

Mass Spectrometry. Electrospray ionization mass spectra were acquired on a Finnigan-MAT SSQ700 (San Jose, Calif.) mass spectrometer fitted with an Analytica of Branford electrospray interface. Electrospray voltages of 2400–3400 V were utilized. Samples were dissolved in either acetonitrile or dichloromethane at concentrations of approximately 10 pmol/l and were introduced into the ESI interface prior to data acquisition by direct infusion at a flow rate of 1 l/min and were introduced prior to data acquisition. Positive ion electron impact ionization (70 ev) MS experiments were performed on a Finnigan-MAT 4615 quadrupole mass spectrometer in conjunction with an INCOS data system. The ion source temperature was 150C and the manifold chamber temperature was 100C. Sample introduction was by means of a gas chromatograph or a direct insertion probe. Positive ion fast atom bombardment mass spectra were acquired on a Finnigan-MAT 212 magnetic sector instrument in combination with an INCOS data system. The accelerating voltage was 3 kV and the ion source temperature was approximately 70C. An Ion Tech saddle field fast atom gun was employed with xenon at 8 keV. Thioglycerol was utilized as the FAB matrix. Positive ion electron impact ionization (70 eV) MS/MS experiments were performed on a Finnigan-MAT TSQ/700 tandem quadrupole mass spectrometer. Sample introduction was by means of a direct insertion probe. The ion source was maintained at 150C and the manifold chamber was held at 70C. Collision-induced dissociation (CID) was achieved by introducing argon into the center rf-only collision octapole until the pressure in the manifold reached 0.9–2.5 ×10$^{-6}$ Torr. The nominal ion kinetic energy for CID product ions was <35 eV (laboratory reference). High resolution data were obtained on a JEOL JMS AX-505H double focusing mass spectrometer in the EB configuration using a resolution of 7500. Sample introduction was by means of a gas chromatograph or direct insertion probe. During mass spectral acquisition, perfluorokerosene was introduced into the ion source by means of a heated inlet. Exact mass assignments were obtained by computer-assisted interpolation from the masses of perfluorokerosene. GC/MS conditions: column, 20 m×0.25 mm DB-1701 (J & W Scientific); carrier gas, helium with a linear velocity of 40 cm/sec; injector, 125C; column temperature, 35C for 3 min, followed by an increase at 10C/min to 100C; injection, split mode, appx. 50:1 ratio.

Spectroscopic Methods. 300 MHz $^1$H NMR spectra and 75 MHz $^{13}$C NMR spectra were obtained on an IBM AF300 instrument using an Oxford Superconducting magnet system, data acquisition was controlled by Bruker software. Infrared spectra were obtained on a Mattson Galaxy Series 5000 FTIR spectrometer controlled by a Macintosh II computer. UV/vis spectra were obtained on a Hewlett Packard 8452A spectrophotometer driven by a Zenith Z-425/SX computer. Conventional X-Band EPR spectra were recorded on a Bruker ER300 spectrometer equipped with an Oxford ESR-900 helium flow cryostat. Mossbauer spectra were obtained on constant acceleration instruments and isomeric shifts are reported relative to an iron metal standard at 298K. In order to avoid orientation of polycrystalline samples by the applied magnetic field, the samples were suspended in frozen nujol.

Syntheses of Macrocyclic Tetraamido-N Donors Ligands

General Reaction Scheme

Depicted below is the preferred reaction sequence for synthesizing the inventive macrocyclic tetraamido ligands:

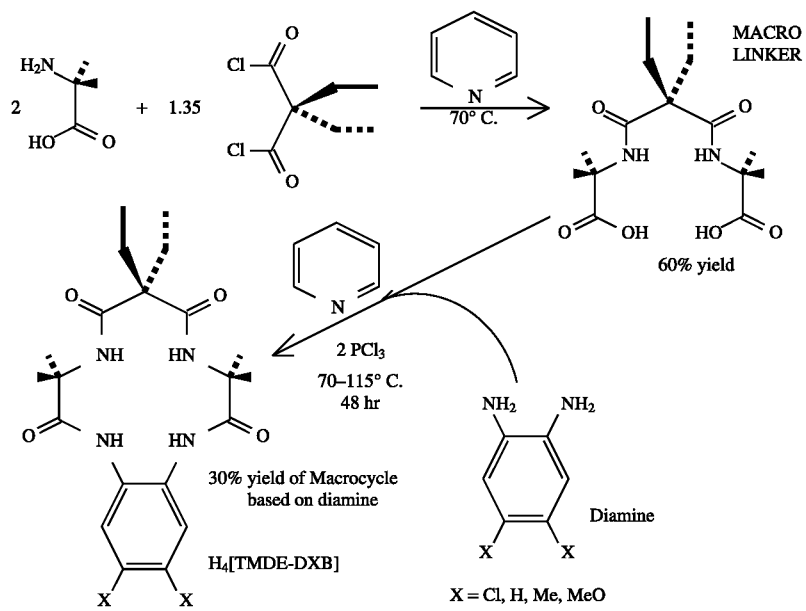

An α-amino carboxylic acid is mixed with an activated malonate in pyridine at temperatures less than 70° C. After the selective double coupling reaction is complete, 72–144 hrs, the MACRO LINKER (A-L-A) is isolated. In a second step a diamine, preferably an o-phenylene diamine is added to a pyridine solution of the MACRO LINKER in the presence of a coupling agent, preferably PCl$_3$ or pivaloyl chloride. The ring closure (a double coupling) reaction is allowed to proceed at reflux for 48–110 hrs, and then the desired macrocyclic tetraamide is isolated in good yield.

In the following Examples 1–25, various portions of the reaction steps are portrayed. Examples 26–32 demonstrate performance attributes and advantages of the invention.

EXAMPLE 1

Macro Linker Intermediate (A-L-A) synthesis, from α-methyl alanine and diethyl malonyl dichloride (a Tetramethyl Diethyl substituted intermediate)

A two-neck flask (1L) fitted with a pressure equalizing addition funnel (250 mL) and a septum is placed under N$_2$. α-amino isobutyric acid (i.e. α-methyl alanine) (20.62 g, 0.2 mol) and dry pyridine (250 mL, dried over 4 Å mol sieves) are added to the flask and heated 60–70C with stirring, then diethyl malonyl dichloride (23.23 mL, 0.135 mol) dissolved in dry pyridine (100 mL, dryed over 4 Å mol sieves) is added to the addition finnel. The contents of the addition funnel are added (dropwise, 1 h) to the reaction and the acylation allowed to proceed (60–70C, 30–36 h) under $N_2$ or with a drying tube fitted. Once the acylation is complete the reaction is quenched by adding $H_2O$ (30 mL) and stirring (60–70C, 24 hrs). The solvent volume is reduced on the rotary evaporator to give an oil, then HCl (conc., ca. 25 mL) is added to a final pH of 2–3. The hot solution is set in the refrigerator (4° C., 15 h), and the resulting tan product collected by frit filtration, and washed thoroughly with acetonitrile (2×100 mL). The air-dried white product, (16.5–19.8 g, 50–60% yield) should be stored in a dessicator. This product is usually pure enough for ring closure reactions, but recrystallization may occasionally be required. Characterization: $^1H$ NMR spectrum ($d^5$-pyridine) [ppm]: 8.9 (s, 2H, NH amide); 2.2 (q, 4H) 1.8 (s, 12H); 1.2 (t, 6H). IR(Nujol mull): [$cm^{-1}$]=3310 (amide NH); 1721 (carboxylic CO), 1623 (amide CO). Anal. Calcd for $C_{15}H_{21}N_2O_6$: C, 54.53; H, 7.93; N, 8.48. Found: C, 54.48; H, 7.88; N, 8.47.

EXAMPLE 2

Large Scale, Macro Linker Intermediate (A-L-A) synthesis, from ax-methyl alanine and diethyl malonyl dichloride (a TMDE substituted intermediate)

A two-neck flask (2L, RB+Claisen) fitted with a pressure equalizing addition funnel (250 mL) and septa, is placed under $N_2$. α-aminoisobutyric acid (i.e. α-methyl alanine) (90.3 g, 0.9 mol) is added, anhydrous pyridine (1.4L, sure seal) is cannulated into the flask and the reaction mix heated to 45–55C and stirred. Pyridine (100 mL, sure seal) and then diethyl malonyl dichloride (104.4 mL, 0.61 mol) are cannulated into the addition funnel. The contents of the addition funnel are added (dropwise, 3–4 h) to the reaction, the addition funnel is then removed, and the acylation allowed to proceed (55°–65° C., 120–130 h) under $N_2$. Once the acylation is complete the reaction is quenched by adding $H_2O$ (100 mL) and stirring (60°–70° C., 24–36 hrs). The solvent volume is reduced on the rotary evaporator to give an oil, then HCl (conc., ca. 110 mL) is added to a final pH of 2–3. The hot solution is set in the refrigerator (4° C., 15 h), and the resulting tan product collected by frit filtration, and washed thoroughly with acetonitrile (700 mL, 150 mL) by stirring in an erlenmeyer flask. The air-dried white product (87.9 g, 60% yield), is crushed in a mortar and pestle and stored in a dessicator. The large scale reaction amide intermediate product is more likely to need recrystallization before use in ring closure reactions.

EXAMPLE 3

Recrystallization of the TMDE substituted intermediate from above

Crude TMDE intermediate from Example 2 (50.4 g, 0.153 mol) is dissolved in $H_2O$ (500 mL, deionized) by adding $Na_2CO_3$ (16.2 g, 0.153 mol) in three aliquots slowly and carefully to avoid excessive frothing, with good stirring and mild heating. The solution is brought to a boil, filtered and acidified with HCl (conc., 30 mL, 0.36 mol). The solution is allowed to cool (overnight, 4° C.) and the white precipitate filtered off and washed with acetonitrile (250 mL). The air dryed product (38.8–45.4 g, recryst. yield 77–90%) should be stored in a dessicator.

EXAMPLE 4

Hexa Methyl (HM) Intermediate (A-L-A)

The synthesis of the HM intermediate is identical to that for the TMDE intermediate in Example 2 with the following exceptions, dimethyl malonyl dichloride (17.8 mL, 0.135 mol) is substituted for diethyl malonyl dichloride, and the reaction temperature must be decreased to 55°–65° C. due to the lower boiling point of the acylating agent. The yield of hexamethyl intermediate is 45–60%. Characterization: $^1H$ NMR ($d^5$ pyridine, [ppm]); 9/2–9.8 br s, 2 H (carboxylic OH), 8.23 s, 2H (amide), 1.87 s 12H ($CH_3$), 1.74 s 6H ($CH_3$). IR (nujol/NaCl) [$cm^{-1}$]: 3317.0 (amide NH); 1717.9 (carboxylic CO); 1625.7 (amide CO). Anal. (dried at 100° C.) Calcd. for $C_{13}H_{22}N_2O_6$; C 51.63, H 7.34, N 9.27. Found; C 51.64, H 7.35, N 9.33.

EXAMPLE 5

Recrystallization of HM Intermediate

Crude hexamethyl (HM) intermediate was recrystallized in the same manner as the TMDE amide intermediate. Due to the slightly higher water solubility of the HM amide intermediate a little less $H_2O$ should be employed.

EXAMPLE 6

Di CyHex Di Ethyl Intermediate

A round bottom flask (500 mL), is charged with 1-amino-1-cyclohexane carboxylic acid (15 g, 0.1 mol), then fitted with a pressure equalizing addition funnel (40 mL), capped with a septum, and purged with nitrogen. Anhydrous pyridine (300 mL) is cannulated into the reaction flask through the addition finnel, and 20 mL into the addition funnel. Start heating the system and stabilize the temperature at 60° C. Once 60° C. is reached, one-third of the total diethyl malonyl dichloride to be utilized in the reaction (i.e. 6 mL, 0.033 mol) is added via syringe to the addition flask. The mixture of pyridine/diethyl malonyl dichloride is added dropwise to the reaction and the acylation allowed to proceed for 12 hours. A second (6 mL, 0.033 mol) and third aliquot (6 mL, 0.033 mol) are added at 12 hour intervals. After all of the acylating agent has been added and allowed to react (total reaction time 48–56 h), 20 mL of water is added dropwise to the reaction. The reaction is heated for an additional 24 hours to ring open the mono and bis oxazalone intermediates and yield the diamide dicarboxylic acid. Removal of the pyridine by rotary evaporation yields a pale yellowish tan sludge which is acidified to pH 2 with HCl (conc.). The crude product is collected by filtration, washed with acetonitrile and air dried to yield the white DiCyHexDE-amide intermediate (16 g, 74%). Characterization: $^1H$ NMR ($d^5$-pyridine) [ppm]: 8.30 (s, 2H, NH amide), 2.60 (m, 4H, cyhex), 2.25 (q, 4H, ethyl $CH_2$), 2.15 (m, 4H, cyhex), 1.8–1.5 (m, 10H, cyhex), 1.25 (m, 2H, cyhex), 1.20 (t, 6H, ethyl $CH_3$). $^{13}C$ NMR broadband decoupled ($d^5$-pyridine) [ppm]: 178.0, (carboxylic CO), 174.3 (amide CO), 60.5 (cyhex quat), 59.4 (malonyl quat), 33.0 (cyhex $CH_2$), 30.3 (ethyl $CH_2$), 26.0 (cyhex $CH_2$), 22.3 (cyhex $CH_2$), 9.9 (ethyl $CH_3$). IR (nujol/NaCl) [$cm^{-1}$]: 3307 (amide NH); 3150 (sh, br, m, amide NH/carboxylic OH), 3057 (s, str, H bonded amide NH/carboxylic OH), 1717 (s, str, carboxylic CO); 1621 (s, str, amide CO). Anal. Calcd for $C_{21}H_{34}N_2O_6$: C, 61.44; H, 8.35; N, 6.82. Found: C, 61.41; H, 8.38; N, 6.90%.

EXAMPLE 7

Di CyHex Diethyl Mono Oxazalone

Failure to quench the Di CyHex Di Ethyl Intermediate Reaction (with heat & water, see above) at a stoichiometry of 1.35 diethyl malonyl dichloride: 2 Cy Hex amino acid, leads to a mixture of the DiCyHexDE-amide intermediate and mono oxazalone products. The DiCyHexDE Mono Oxazalone product is moderately soluble in boiling cyclohexane while the cyclohexyl amide intermediate is not, allowing for a simple separation of the product mixture. utilized in the reaction (i.e. 6 mL, 0.033 mol) is added via syringe to the addition flask. The mixture of pyridine/diethyl malonyl dichloride is added dropwise to the reaction and the acylation allowed to proceed for 12 hours. A second (6 mL, 0.033 mol) and third aliquot (6 mL, 0.033 mol) are added at 12 hour intervals. After all of the acylating agent has been added and allowed to react (talone ca. 4 g. Characterization of the mono oxazalone: $^1$H NMR (d$^5$-pyridine) [ppm]: 9.7 (s, 1H, amide NH), 2.7–1.6 (unresolved Cy Hex groups), 1.05 (t, 6H, ethyl CH$_3$). IR (nujol/NaCl) [cm–1]: 3309 (sh, w, amide NH); 3229 (s, str, H bonded amide NH/carboxylic OH), 3166 (s, str, amide NH/carboxylic OH), 3083 (s, str, H bonded amide NH/carboxylic OH), 1834 (s, str, oxaz C=O), 1809 (s, m, H bonded oxaz C=O), 1743 (s, str, carboxylic CO), 1663 (s, str, oxaz C=N), 1639 (s, br, str, amide CO). Anal. Calcd for $C_{21}H_{32}N_2O$, $(C_6H_{12})0.25$: C, 65.35; H, 8.53; N, 6.77. Found: C, 65.07; H, 8.67; N, 6.68%. Presence of solvate cyclohexane was confirmed by $^{13}$C NMR.

Macrocyclization Reactions

Examples of several synthetic routes for the preparation of macrocyclic tetraamido ligands follow.

Phosphorus Trichloride Coupling

Phosphorus trichloride coupling of the amide-containing intermediate (A-L-A) to aromatic 1,2-diamines yields macrocyclic tetraamides safely, cheaply and in high yield. Two distinct variations of the PCl$_3$ coupling method are useful, the differences relate to the order of addition and choice of reagents utilized. These methods are applicable to the preparation of a wide variety of different macrocycles with different electronic substituents present on the bridge diamine, or steric substituents present on the amide intermediate, primarily because of the parallel incorporation of the macro linker type of amide intermediates into all of the syntheses.

EXAMPLE 8

A. Macrocycle Synthesis via PCl$_3$ Coupling

A long neck flask (250 mL) is charged with the amide intermediate of Examples 2–7, (10 mmol) a stir bar and then baked in the oven (80°–100° C., 30–45 mins). The hot flask is placed under N$_2$, aryl diamine (10 mmol) is added and anhydrous pyridine (50 mL, sure seal) cannulated in. The flask is heated (50°–60° C.) and PCd, (d=1.574 g/mL, 1.72 mL, 20 mmol) syringed in as quickly as possible without excessive refluxing. This is an exothermic reaction, so caution should be used. The temperature is then increased to reflux or just below reflux (100°–1 15° C.) and the reaction allowed to proceed under N$_2$ (48 h). After the acylation is complete, the contents of the flask are acidified with HCl (1 eq., ca. 60 mL) to a final pH 2. The mixture is transferred to an erlenmeyer (water is used to rinse the flask) and stirred with CH$_2$Cl$_2$ (300 mL, 2–3 h), then extracted with additional CH$_2$Cl$_2$ (2×150 mL). The combined organic layers are washed with dilute HCl (0.1M, 2×100 mL) followed by dilute aqueous Na$_2$CO$_3$ (2×5 g/100 mL). The organic solvents are removed on the rotary evaporator to yield crude product (30%). The weight of crude product is usually equivalent to the initial weight of diamine.

B. Macrocycle Synthesis via PCl$_3$ Coupling

A long neck flask (250 mL) is charged with MgSO$_4$ (5 g), a stir bar, aryl diamine (10 mmol) and pyridine (50 mL, dryed over 4 Å mol sieves) then placed under N$_2$. PCl$_3$ (d=1.754 g/mL, 1.72 mL, 20 mmol) is added via syringe and the mixture brought to reflux for 30 mins, an orange/yellow precipitate forms. The mixture is cooled somewhat, an amide intermediate (10 mmol) is added, then the mixture is refluxed under N$_2$ (115° C., 48 h). After the acylation is complete, the contents of the flask are acidified with HCl (1 eq., ca. 60 mL) to a final pH 2. The mixture is transferred to an erlenmeyer and stirred with CH$_2$Cl$_2$ (300 mL, 2–3 h), then extracted with additional CH$_2$Cl$_2$ (2×150 mL). The combined organic layers are washed with dilute HCl (0.1M, 2×100 mL) followed by dilute Na$_2$CO$_3$ (2×5 g/100 mL). The organic solvents are removed on the rotary evaporator to yield crude product (30%). The weight of crude product is usually equivalent to the initial weight of diamine.

Note: For larger scale macrocyclization reactions, the ring closure times are increased to 4–5 days at reflux, and most of the pyridine present at the end of the reaction is removed via rotary evaporation prior to acidification.

EXAMPLE 9

TMDE-DCB from TMDE Intermediate+DCB Diamine 1,2-Diamino-4,5-dichlorobenzene (1.77 g, 10 mmol) was utilized as the aryl diamine with TMDE amide intermediate (3.3 g, 10 mmol) in the PCl, method A or B macrocyclization reaction. The crude macrocyclic product (2.7 g) was recrystallized from a minimum amount of hot 95% EtOH by evaporation to yield pure TMDE-DCB (1.5 g, 32%). Characterization: $^1$H NMR (CD$_2$Cl$_2$) [ppm]:7.65 (s, 1H, ArH), 7.35 (s, 2H, amide NH), 6.45 (s, 2H, amide NH), 1.90 (q, 4H, ethyl CH$_2$), 1.57 (s, 12H, RCH$_3$), 0.85 (t, 6H, ethyl CH$_3$). IR (nujol/NaCl) [cm$^{-1}$]: 3454 (trace ROH), 3346 (br, amide NH), 1706&1688&1645 (amide CO). Anal.Calcd. for $C_{21}H_{28}Cl_2N_4O_4$; C, 53.51; H, 5.99; N, 11.89. Found C, 53.58; H, 6.09; N, 11.89.

EXAMPLE 10

TMDE-B from TMDE Intermediate+B Diamine 1,2-Diaminobenzene (i.e. o-phenylene diamine)(1.08 g, 10 mmol) was utilized as the aryl diamine with the TMDE amide intermediate (3.3 g, 10 mmol) in the PCl, method A or B macrocyclization reaction. The crude macrocyclic product (1.5 g) was recrystallized from a minimum amount of hot 95% EtOH by evaporation to yield pure TMDE-B (25% from diamine). Characterization: $^1$H NMR (CDCl$_3$) [ppm]: 7.55 (m, 2H, ArH), 7.48 (s, br, 2H, aryl amide NH), 7.17 (m, 2H, ArH), 6.46 (s, br, 2H, alkyl amide NH), 2.07 (m, br, 4H, ethyl CH$_2$), 1.60 (s, 12H, RCH$_3$), 0.89 (t, 6H, ethyl CH$_3$. IR (nujol/NaCl) [cm$^{-1}$]: 3395&3363 (amide NH), 1702&1680&1652&1635 (amide CO). Anal. Calcd. for $C_{21}H_{30}N_4O_4$. H$_2$O: C, 59.98; H, 7.67; N, 13.32. Found: C, 60.18; H, 7.20; N, 13.18.

EXAMPLE 11

TMDE-DMB from TMDE Intermediate+DMB Diamine 1,2-Diamino-4,5-Dimethylbenzene (1.36 g, 10 mmol) was utilized as the aryl diamine with Tetramethyl Diethyl amide intermediate (3.3 g, 10 mmol) in the PCl$_3$ method A or B macrocyclization reaction. The crude macrocyclic product (1.6 g) was recrystallized from a minimum amount of hot 95% EtOH by evaporation to yield pure TMDE-DMB (25% from diamine). Characterization: $^1$H NMR (DMSO d$^6$) [ppm]: 8.00 (s, 2H, amide NH), 7.67 (s, 2H, amide NH), 7.28 (s, 2H, ArH), 2.17 (s, 6H, aryl CH$_3$), 1.99 (q, 4H, ethyl CH$_2$), 1.46 (s, 12H, RCH$_3$), 0.75 (t, 6H, ethyl CH$_3$). IR (nujol/NaCl) [cm$^{-1}$]: 3446 (s, m, trace ROH), 3362 (s, str, amide NH), 3348 (sh, m, amide NH), 3332 (s, str, H amide NH), 1696 (amide CO), 1679 (amide CO), 1651 (amide CO), 1641 (amide CO), 1584 (s, m/w, aryl ring/amide). Anal. Calcd. for $C_{23}H_{34}N_4O_4$: C, 64.16; H, 7.96; N, 13.01, Found: C, 64.09, 64.28; H, 8.04, 7.92; N, 12.86, 13.04.

EXAMPLE 12

TMDE-DMOB from TMDE Amide Intermediate+ DMOB Diamine 1,2-Diamino-4,5-Dimethoxybenzene 0.2 HBr (5.0 g, 15 mmol) prepared as above was utilized as the aryl diamine directly with the Tetramethyl Diethyl amide intermediate (5.0 g, 15 mmol) in a 1.5 scale PCl$_3$ method A or B macrocyclization reaction. The crude macrocyclic product (3.57 g) was recrystallized from a minimum amount of hot 80–85% EtOH (1 g/40 mL) by evaporation to yield pure TMDE-DMOB (30% from diamine). Characterization: $^1$H NMR (CD$_2$Cl$_2$) [ppm]: 7.26 (s, 2H, amide NH), 7.01 (s, 2H, ArH), 6.41 (s, 2H, amide NH), 3.80 (s, 6H, aryl OCH$_3$, 2.07 (q, br, 4 H, ethyl CH$_2$, 1.54 (s, 12H, RCH$_3$), 0.90 (t, 6H, ethyl CH$_3$). IR (nujol/NaCl) [cm$^{-1}$]: 3451 (s, m, H bonded H$_2$O), 3391&3347 (amide NH), 1695&1670&1655 (amide CO). Anal. Calcd. for $C_{23}H_{34}N_4O_6$, $(H_2O)_{0.33}$: C, 58.96; H, 7.46; N, 11.96, Found (ESU); C, 58.90; H, 7.26; N, 11.76. Presence of solvate H$_2$O was confirmed by $^1$H NMR and IR.

EXAMPLE 13

TMDE-Nap from TMDE Intermediate+Nap Diamine 4,5 Diamino Naphthalene (1.68 g, 10 mmol) was utilized as the aryl diamine with the Tetramethyl Diethyl amide intermediate (3.3 g, 10 mmol) in the PCl$_3$ method A or B macrocyclization reaction. Unoptimized yield was 15–20% from diamine. $^1$H NMR (CDCl$_3$) [ppm]: 8.05 (s, 2H, ArH ring), 7.75 (m, 2H, ArH ring), 7.55 (s, 2H, Ar amide NH), 7.35 (m, 2H, ArH' ring), 6.45 (s, 2H, alkyl amide NH), 2.15 (m, br, 4H, ethyl CH$_2$), 1.65 (s, 12H, RCH$_3$), 0.90 (t, 6H, ethyl CH$_3$.

EXAMPLE 14

HM-DCB from HM Intermediate+DCB Diamine 1,2-Diamino-4,5-Dichlorobenzene (1.77 g, 10 mmol) was utilized as the diamine with Hexa Methyl amide intermediate (3.02 g, 10 mmol) in the PCl$_3$ method A or B macrocyclization reaction. The crude macrocycle (1.33 g, 30%) was recrystallized from a minimum of hot n-propanol by evaporation, 1st crop recrystallization yield was 60%. Characterization: $^1$H NMR [ppm]: 7.69 (s, 2H, ArH), 7.39 (s, 2H, amide NH), 6.44 (s, 2 H, amide NH), 1.58 (s, 12H, arm methyls), 1.53 (s, 6H, malonate methyls), small n-propanol peaks were noted. IR (nujo/NaCl) [cm$^{-1}$]: 3503 (s, br, m-w, n-propanol OH), 3381 (sh, m, amide NH), 3338 (s, str, amide NH), 1689 (s, str, amide CO), 1643 (s, str, amide CO). Anal. Calcd. for $Cl_9H_{24}N_4O_4Cl_2 \cdot (C_3H_8O)_{0.2}$: C, 51.70; H, 5.57, N 12.30% Found C, 51.69; H, 5.63; N, 12.33%.

EXAMPLE 15

HM-DMOB and HM-B from HM Intermediate+ DMOB or B Diamine

The HM intermediate has also been used to synthesize HM-B and HM-DMOB according to the same method and with similar results to those obtained in example 14 for the dichloro derivative. $^1$H NMR data for HM-DMOB in CDCl$_3$ [ppm]: 7.65 (s, 2H, amide NH), 7.21 (s, 2H, aryl CH), 6.72 (s, 2H, amide NH), 4.00 (s, 6H, methoxy CH$_3$), 1.76 (s, 12H, arm methyls), 1.58 (s, 6H, malonate methyls). $^1$H NMR data for HM-B in d$^5$ pyridine [ppm]: 8.55 (s, 2H, amide NH), 8.40 (s, 2H, amide NH), 7.81 (m, 2H, ArH aa'bb'), 7.10 (m, 2H, ArH aa'bb'), 1.77 (s, 12H, arm methyls), 1.73 (s, 6H, malonate methyls). The amide peaks tend to shift a few tenths of a ppm in the presence of impurity species such as water, acids etc.

EXAMPLE 16

DiCyHexDE-DCB from DiCyHexDE Intermediate+ DCB Diamine 1,2-Diamino-4,5-Dichlorobenzene (1.77 g, 10 mmol) was utilized as the aryl diamine with Di Cy Hex Diethyl amide intermediate (3.3 g, 10 mmol) in the PCl$_3$ method A or B macrocyclization reaction. Due to the increased steric hindrance an increased ring closure reaction time is recommended (3–4 days as opposed to the usual 48 h). Cy Hex Oxazalones formed as a side product during the reaction are not removed by the acid base workup, so it is necessary to triturate/wash the initially isolated CH$_2$Cl$_2$ soluble product with pentane to remove the oxazalones. Evaporation of the pentane washes allows for recycling of the oxazalones. The crude pentane insoluble product was recrystallized by dissolving in CH$_2$Cl$_2$ or CHCl$_3$, adding cyclohexane until slightly cloudy and then evaporating in air (1–2 days) to yield the white microcrystalline DiCyHexDE-DCB product, which was collected by filtration (1.38 g, 25% from diamine). Recrystallization from hot neat toluene with evaporation also appears promising. Characterization: $^1$H NMR (CDCl) [ppm]: 7.70 (s, 2H, ArH), 7.45 (s, 2H, amide NH), 6.45 (s, 2H, amide NH), 2.35 (m, br, 4H, cyhex), 2.00 (m, br, 8H, cyhex/ethyl CH$_2$), 1.70 (m, br, 8H, cyhex), 1.30 (m, br, 4H, cyhex), 0.90 (t, 6H, ethyl CH$_3$). Anal. (Dryed at 100C) Calcd. for $C_{27}H_{36}Cl_2N_4O_4$, $(C_6H_{12})_{0.2}$: C, 59.60; H, 6.81; N, 9.86, Found: C, 59.60; H, 6.77; N, 9.77. Presence of solvent cyclohexane was confirmed by $^1$H and $^{13}$C NMR.

EXAMPLE 17

DiCyHexDE-B from DiCyHexDE Intermediate+B Diamine 1,2-Diaminobenzene (ortho-phenylene diamine, 1.08 g, 10 mmol) was utilized as the aryl diamine in a preparation analogous to that for DiCyHexDE-DCB, to yield DiCyHexDE-B (1.25 g, 26% from diamine). Characterization: $^1$H NMR (CD$_3$CN) [ppm]: 7.62 (s, 2H, aryl amide NH), 7.51 (m, 2H, ArH), 7.18 (m, 2H, ArH), 6.71 (s, 2 H, alkyl amide NH), 2.12 (m, 6H, Cyhex), 1.85 (q&m, ethyl CH$_2$ & cyhex), 1.62 (m, cyhex), 1.37 (m, cyhex), 0.90 (t, 6H, ethyl CH$_3$), 0.85 (m, cyhex). IR (nujol/NaCl) [cm$^{-1}$]: 3570 (s, m, H$_2$O), 3385 (s, str, amide NH), 314 (s, str, amide NH), 3258 (s, m, br, H bonded amide NH), 1694 (s, str, amide CO), 1651 (s, str, amide CO), 1594 (s, m, aryl ring/amide).

EXAMPLE 18

Di CyHex Diethyl Bis Oxazalone

This product was obtained as a byproduct of the PCl$_3$ macrocyclization reaction of Di CyHex Di Ethyl Amide Intermediate with o-phenylene diamine. The bis oxazalone is not removed by the acid base workup (it is a neutral molecule and very organic soluble). Washing of the crude macrocyclic/oxazalone product with pentane extracts most of the bis oxazalone into the pentane. Air evaporation of the pentane layer yields the pure bis oxazalone as large (1 cm×1 cm×0.5 cm) transparent prisms. Due to the bulky hydrophobic CyHex groups this oxazalone is much more resistant to hydrolysis than the corresponding methyl derivative. Characterization of the bis oxazalone: $^1$H NMR (CD$_3$CN) [ppm]: 2.05 (q, 4H, ethyl CH$_2$), 1.8–1.4 (Unresolved Cy Hex Groups), 0.88 (t. t H, ethyl CH$_3$). $^{13}$C NMR broadband decoupled (CD$_3$CN) [ppm]: 181.0 (oxaz C=O), 162.7 (oxaz C=N), 69.0 (oxaz cyhex quat), 49.0 (malonate quat), 34.3 (cyhex methylenes), 25.5 (cyhex methylenes), 24.9 (malonate methylenes), 21.8 (cyhex methylenes), 8.3 (ethyl CH$_3$). IR (nujol/NaCl) [cm$^{-1}$]: 1822 (s, str, br, oxaz C=O), 1662 (s, str, oxaz C=N). Anal. (Dryed at 50C) Calcd. for C$_{21}$H$_{30}$N$_2$O$_4$; C, 67.36; H, 8.07; N, 7.48, Found: C, 67.26; H, 8.15; N, 7.64.

Synthesis of Chelate Complexes

EXAMPLE 19

[LN]2 and [Et$_4$N]3. [the tetraethylammonium salts of iron(III) chloro TMDE-DCB monoanion and iron(III) aquo TMDE-DCB monoanion respectively]

The parent macrocyclic tetraamide of any of Examples 10–18 above (525 mg, 1.1 mmol) is dissolved in tetrahydrofuran (40 mL, Aldrich) under N$_2$. Using schlenk techniques, tert-butyllithium (2.6 mL, 4.4 mmol, 1.7M in 2,4-dimethylpentane, Aldrich) was added to the solution under N$_2$ at −108° C. Ferrous chloride (anhydrous, 155 mg, 1.2 mmol, Alfa) was then added and the solution warmed to room temperature with stirring (16 h), to yield an olive-green precipitate, an air sensitive Fe$^{11}$ complex. Air was admitted through a drying tube (2 h), and the orange solid was collected and washed with CH$_2$Cl$_2$ (2×10 mL). The resulting orange powder was dried under reduced pressure. Yield: 595 mg (93%). Because of variable solvation and limited solubility, the lithium salt was converted to the tetraethylammonium salt for further use. The lithium salt (595 mg) in CH$_3$OH (50 mL) was loaded on an ion exchange column (Dowex® 50X2-100, 25 g, 2 cm×12.5 cm) that had been presaturated with [Et$_4$N]$^+$ cations, and the orange band was eluted with CH$_3$OH (100 mL). The solvent was removed under reduced pressure. The residue was suspended in CH$_2$Cl$_2$ (20 mL) and the mixture was filtered. The solvent was removed from the mother liquor under reduced pressure giving an orange hygroscopic glassy residue of [Et$_4$N]2 that was used without further purification. IR (Nujol/NaCl, cm$^{-1}$): 1619 ((CO)amide), 1575 ((CO)amide), 1534 ((CO)amide). Careful purification of an iron(III) starting material was more conveniently approached by dealing with the axial aqua monoanionic complex rather than this axial chloro dianionic complex. [Et$_4$N]2 (550 mg, ca. 0.7 mmol) was dissolved in CH$_3$CN (50 mL). Silver tetrafluoroborate (140 mg, 0.7 mmol) was dissolved in CH$_3$CN (2 mL) and was added to the solution which was stirred (1 h). The AgCl precipitate was filtered off and the solvent removed under reduced pressure. The resulting [Et$_4$N]3 was further purified by elution through a silica gel column (8% MeOH in CH$_2$Cl$_2$). The solvent was removed under reduced pressure and the product was recrystallized from H$_2$O. Yield: 360 mg (77%, variable solvation with water was found in different microcrystalline samples). IR (Nujol/NaCl, cm$^{-1}$): 1590 ((CO)amide), 1565 ((CO)amide), 1535 ((CO)amide). Anal. Calcd for C$_{29}$H$_{46}$N$_5$FeO$_5$Cl$_2$. (H$_2$O): C, 50.52; H, 7.02; N, 10.16.: Cl, 10.28. Found: C, 50.24; H, 6.84; N, 9.82; Cl, 10.32. ESIMS (negative ion): m/z 522.2, [3−H$_2$O]$^{1-}$ (100%); m/z 269.7, [3−H$^+$]$^{2-}$ (18%).

EXAMPLE 20

[Et$_4$N]4. [the tetraethylammonium salt of iron(IV) chloro TMDE-DCB monoanion]

[Et$_4$N]2 (500 mg, ca. 0.6 mmol) was dissolved in CH$_2$Cl$_2$ (30 mL). Ammonium cerium(IV) nitrate (10.3 g, 18.3 mmol) was added to the solution and the mixture was stirred (2 h). The solid cerium salts were removed by filtration. The purple product was obtained by removing the solvent under reduced pressure and drying under vacuum. Yield: 400 mg (95%). Purple crystals were obtained by recrystallization from CH$_2$Cl$_2$/Et$_2$O. IR (Nujol/NaCl, cm$^{-1}$): 1688 ((CO) amide), 1611 ((CO)amide), 1582 ((CO)amide). ESIMS (negative ion): m/z 557, [4]$^{-1}$ (100%); m/z 522, [4−Cl]$^{1-}$ (65%).

EXAMPLE 21

Synthesis of [Ph$_4$P]5 [the tetraphenylphosphonium salt of iron(IV) cyano TMDE-DCB monoanion] from [Et$_4$N]4 [the tetraethylamunonium salt of iron (IV) chloro TMDE-DCB monoanion] and NaCN

[Et$_4$N]4 [the tetraethylammonium salt of iron(IV) chloro TMDE-DCB monoanion] (225 mg, 0.33 mmol) was suspended in H$_2$O (10 mL). Sodium cyanide (140 mg, 2.85 mmol) was dissolved in H$_2$O (10 mL) and added to the suspension and the mixture was sonicated (Branson 1200, 0.5 h). The purple suspension changed to a deep blue solution and nearly all the solid material dissolved. The mixture was filtered and the blue product was precipitated by adding PPh$_4$Cl [tetraphenylphosphonium chloride] dissolved in water (600 mg, 1.6 mmol, 10 mL, Aldrich). The blue precipitate was collected and washed with H$_2$O (2×10 mL). Yield: 250 mg (0.28 mmole, 85%). This material (120 mg) was further purified by thin layer chromatography (TLC) (Silica gel plate, GF, 20 cm×20 cm×1000 m, 10:1 CH$_2$Cl$_2$:CH$_3$CN). The blue material was extracted from the silica gel with CH$_3$CN:CH$_2$Cl$_2$ (1:1, 60 mL). The solvent was removed under reduced pressure and the residue was dissolved in CH$_2$Cl$_2$ (3 mL) and filtered. Addition of pentane (150 mL) gave a blue powder (90 mg, 0.10 mmol) Yield on purification: 75%). IR (Nujol/NaCl, cm$^{-1}$): 2129 ((CN)), 1659 ((CO)amide), 1598 ((CO)amide), 1571 ((CO)amide). Anal. Calcd for: C$_{46}$H$_{44}$N,FeOCl$_2$P: C, 62.18; H, 4.99; N, 7.88; Cl, 7.98. Found: C, 61.96; H, 5.04; N, 7.84; Cl, 8.06. ESIMS (negative ion): m/z 548.2, [5]$^{1-}$ (100%); m/z 522.1, [5−CN]$^{1-}$ (20%). For $^{13}$C-labeled cyanide: m/z 549.2, [5]$^{1-}$ (100%); m/z 522.1, [5−$^{13}$CN]$^{1-}$ (8%).

EXAMPLE 22

The Synthesis of [Ph$_4$P]5 [the tetraphenylphosphonium salt of iron(IV) cyano TMDE-DCB monoanion] from Nitrile Cyanide Sources

[Ph$_4$P]5 [the tetraphenylphosphonium salt of iron(IV) cyano TMDE-DCB monoanion] can be formed in the presence or absence of base. In the absence of base, the blue color fades to yellow-orange as the solvent is removed in the workup procedures. Therefore, product isolation to obtain the blue solid is best carried out in the presence of added base at a pH range of 9–10. The following reaction yields 5 with each of $CH_3CN$, $CD_3CN$, $CH_3CH_2CN$ and $(CH_3)_2CHCN$ as the solvent substrates. Base was not added to the catalytic reactions described. It was demonstrated that the blue compound is an effective catalyst precursor by adding isolated [$Ph_4P$]5 to an acetonitrile solution of TBHP (tertiary butyl hydroperoxide), both the solvent and oxidant were consumed indicating that although [$Ph_4P$]5 is formed as an end product of the catalytic oxidation process it is not a deactivated form of the catalyst.

EXAMPLE 23

The Synthesis of [$Ph_1P$]5 in the Presence of Base

[$Et_4N$]3 (160 mg, 0.23 mmol) was dissolved in the chosen nitrile solvent (6 mL). Tetraethylammonium hydroxide base was added (20 wt %, 0.370 mL, 0.52 mmol, Aldrich), then t-butyl hydroperoxide (90%, 0.605 mL, 5.4 mmol, Aldrich) was added dropwise with stirring (20 min) resulting in a blue solution. The remaining nitrile was removed under reduced pressure, leaving an oily blue residue which was dissolved in $H_2O$ (15 mL) and filtered. The blue material was precipitated from the filtrate by addition of an aqueous solution of $PPh_4Cl$ (800 mg, 2.1 mmol, Aldrich, 10 mL). The blue precipitate was collected and washed with $H_2O$ (2×10 mL). Yield: 130 mg, 0.15 mmol (65%). Further purification was carried out as described in the [P?P]5 section.

EXAMPLE 24

X-ray Crystal Structure Data and Refinement for [$Et_1N$]3 $H_2O$ $C_{29}H_{48}Cl_2FeN_5O_6$, M=689.47, Triclinic, Space group P-1, a=9.899(2); b=11.771(2); c=14.991(4)Å, =95.33(2); =100.09(2); =92.31(2)°, V=1709.6(6)Å$^3$, $D_{obs}$=1.33 g cm$^{-3}$, $D_{calcd}$ (Z=2)=1.339 g cm$^{-3}$, T=293K, =0.71069 Å, =0.64 mm$^{-1}$, trans coeff. 0.87–1.00. Diffraction data were collected at room temperature on an Enraff-Nonius CAD-4 diffractometer using graphite monochromated Mo—K radiation. Three reflections were monitored throughout data collection, only random fluctuations in intensity being observed. The structure was solved by direct methods. Hydrogen atoms bonded to the carbon were included in calculated positions with C|H bond distance of 0.96 Å and were refined using a riding model with a thermal parameter 20% greater than the parent carbon. Hydrogen atoms of the water molecule were located from electron density difference maps and their coordinates allowed to refine with the thermal parameter fixed at 20% greater than that of the oxygen. Refinement was by full-matrix least squares on $F^2$ with scattering factors taken from the International Tables. All non-hydrogen atoms were refined with anisotropic thermal parameters. The final difference maps were featureless. Refinement converged to R=0.053, wR2=0.112 with weights $1.0/[^2(F^{o2})+\{0.0652(F_o^2+2F_c^2)/3\}^2]$ for 2262 observed reflections.

EXAMPLE 25

X-ray Crystal Structure Data and Refinement for [$Et_4N$]4

Single crystals of [$Et_4N$]4. at 20±1C are monoclinic, space group $P2_1/c$-$C^5_{2h}$ (No. 14) with a=9.958(2) Å, b=14.956(3) Å, c=22.688(5) Å, =90.00, =93.83(2), =90.00, V=3372(1) Å$^3$, and Z=4 ($d_{calc}$=1.357 g cm$^{-3}$; $_a$(CuK)=6.17 mm$^{-1}$). A total of 4626 independent absorption-corrected reflections having 2(CuK)<115.0 were collected using $^-$2 scans and Ni-filtered CuK radiation. The structure was solved using "Direct Methods" techniques with the Nicolet SHELXTL software package as modified at Crystalytics Company. The resulting structural parameters have been confined to a convergence of $R_1$(unweighted, based on F)=0.037 for 2680 independent reflections having 2(CuK) <115.0 and I>3(I). The ten methyl groups were refined as rigid rotors with sp$^3$-hybridized geometry and a C—H bond length of 0.96 Å. The initial orientation of each methyl group was determined from difference Fourier positions for the hydrogen atoms. The final orientation of each methyl group was determined by three rotational parameters. The refined positions for the rigid rotor methyl groups gave C—C—H angles which ranged from 103–118. The remaining hydrogen atoms were included in the structure factor calculations as idealized atoms (assuming sp$^2$- or sp$^3$-hybridization of the carbon atoms and a C—H bond length of 0.96 Å) riding on their respective carbon atoms. The isotropic thermal parameter of each hydrogen atom was fixed at 1.2 times the equivalent isotropic thermal parameter of the carbon to which it is covalently bonded.

EXAMPLE 26

Sustained Catalyst Stability

Figure 3:
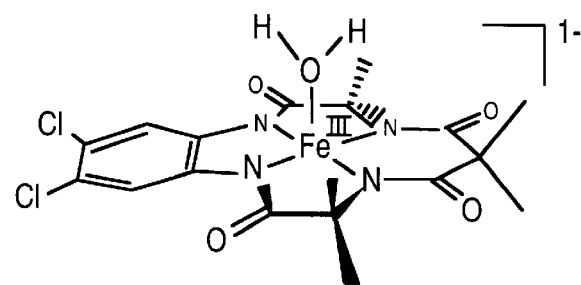
FIG. 3 is a graph comparing the sustained catalyst stability of preferred embodiments of the invention versus control.
Figure 3:
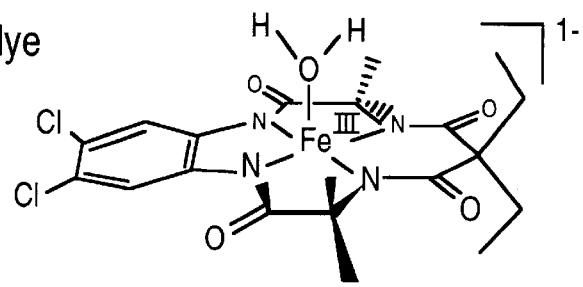
Figure 3:
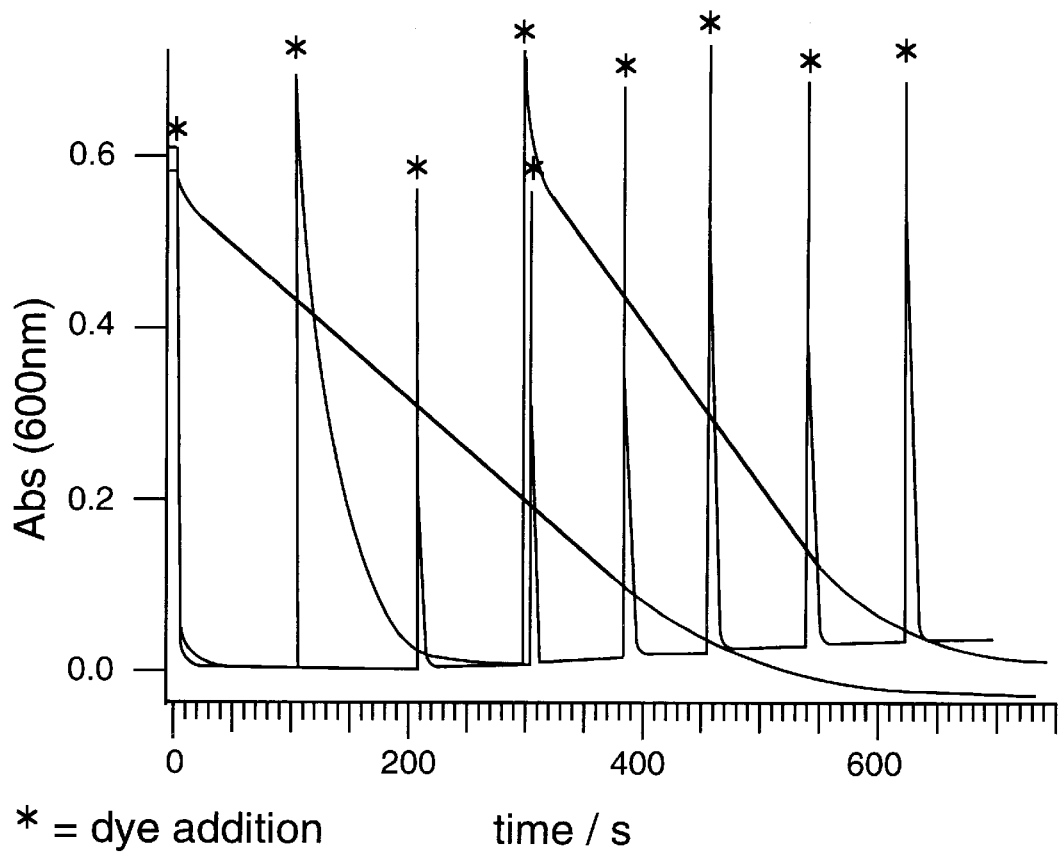

With reference to FIG. 3, the catalytic longevity of two embodiments of the invention were compared. Compound 1 had substituents R' and R" each as $CH_3$, while Compound 2 had substituents R' and R" each as —$CH_2CH_3$. The control was no catalyst added.

The conditions were pH 9, room temperature (21.1° C.), with a buffer system of $NaHCO_3/Na_2CO_3$. Oxidant was 4 mM(30%) $H_2O_2$. At each of the asterisks, 12 µM pinacyanol chloride dye was added.

As can be seen from the graph, each addition of dye where Compound 1 was present resulted in almost immediate decolorization. Compound 2, the diethyl compound, had more gradual decolorization. The control showed only a very gradual rate of decolorization.

From the foregoing, it can be seen that the inventive compounds, and especially Compound 1, are effective in oxidizing and decolorizing extraneous or free flowing dyes released from colored fabrics which are washed in a wash liquor. Thus, the inventive macrocyclic tetraamido compounds provide a unique benefit to an oxidant system, namely dye scavenging, thus preventing the transfer of extraneous and thus, unwanted dyes from one fabric to another in the wash liquor.

Examples 27–30 are further examples of the unique dye transfer inhibition properties of the inventive macrocyclic tetraamido ligands. In Examples 27–28, spectra and absorbance-time curves were recorded on a Shimadzu spectrophotometer. The samples were scanned over the wavelength (λ) range 350 to 700 nm prior to the addition of peroxide or catalyst to determine wavelength for the dye's maximum absorbance. The spectrophotometer was then set to peak wavelength and the peroxide and/or catalyst were added. Changes in the peak absorbance after 2 minutes were reported.

Acid Blue 25 was monitored at 600 nm. The samples were performed at 25° C. in a 1 cm cuvette containing 2ml solution.

EXAMPLE 27

Bleaching of Acid Blue 25 in Solution

To a solution of Acid Blue 25 [120 mg/l (dye content 45%), initial absorbance at 600 nm was 1.2] was added: (a)

20 ppm A.O. $H_2O_2$; (b) 20 ppm A.O. $H_2O_2$+1 ppm of the inventive compound wherein Z and Y are each hydrogen (hereafter "FeB"); and (c) 20 ppm A.O. $H_2O_2$+1 ppm of the inventive compound wherein Z and Y are each chloro (hereafter "FeDCB"). As shown below, only systems containing catalysts gave any bleaching effect of the dye (monitored as observed change in absorbance at 600 nm in two minutes). As a further comparison, the absorbance loss caused by sodium hypochlorite (5.25% solution, added at 20 ppm Av. $Cl_2$). The results are tabulated below:

| Bleaching System | Absorbance Loss after 2 min. |
|---|---|
| 20 ppm $H_2O_2$ | 0 |
| 20 ppm $H_2O_2$ + 1 ppm FeB | 1.15 |
| 20 ppm $H_2O_2$ + 1 ppm FeDCB | 1.15 |
| 20 ppm Av. $Cl_2$ NaOCl | 0 |

A large absorbance loss means more dye has been decolorized. The foregoing data demonstrates that when the inventive catalysts are used, there is efficient dye transfer inhibition. As compared with the amount of dye added (1.2 initial absorbance), the loss of dye is greater than 90% (1.15÷1.2×100%=95.83%).

EXAMPLE 28

Bleaching of Acid Orange 8 in Solution

Experiments were performed as in Example 27, above, except that a solution of Acid Orange 8 (210 mg/l (dye content 65%), initial absorbance at 490 nm was 1.2). Bleaching was measured as change in absorbance at 490 nm.

| Bleaching System | Absorbance Loss after 2 min. |
|---|---|
| 20 ppm $H_2O_2$ | 0 |
| 20 ppm $H_2O_2$ + 1 ppm FeB | 1.15 |
| 20 ppm $H_2O_2$ + 1 ppm FeDCB | 1.15 |
| 20 ppm Av. $Cl_2$ NaOCl | 0.17 |

Once again, as compared with the amount of dye added (1.2 initial absorbance), the loss of dye is greater than 90% (1.15÷1.2×100%=95.83%). As compared with the amount of dye added (1.2 initial absorbance), the loss of dye is greater than 90% (1.151.2×100%=95.83%). The dye transfer ($\Delta E$) was calculated again, in accordance with the procedures set forth in the co-pending application Ser. No. 08/396,853, filed Mar. 1, 1995, of Johnson et al., entitled "LAUNDRY ARTICLE FOR PREVENTING DYE CARRY-OVER AND INDICATOR THEREFOR." $\Delta E$ averages the reflectance changes of an item of fabric prior to and after washing according to the equation set forth therein. An increase in the calculated value of $\Delta E$ for a target fabric washed in the presence of a dye source as compared to a target fabric prior to washing indicates that the target fabric has absorbed the dye. All dyes are from Aldrich Chemicals.

In Examples 29 and 30 below, the following conditions were used: 0.95 g of Ultra Tide® laundry detergent (Procter & Gamble) was added to a Terg-O-Tometer bucket with 1.5 liter of warm water, and two 8×8 inch cotton target fabric (large swatch), and, a fabric that released dye to solution. The purpose of the target fabric was to serve as a dye receptor for any extraneous dye which was not decolorized or oxidized. Samples were agitated for 12 minutes after the addition of the dye scavenging system ($H_2O_2$ and catalyst) using a Terg-O-Tometer followed by a two minute ambient temperature water rinse, and 20 minutes of drying in an automatic dryer.

EXAMPLE 29

Dye transfer from Textile to Textile Using Direct Red 79

In order to demonstrate that the effects seen in the above solution experiments (Examples 27–28) were reflected on textiles present in such solutions, experiments were carried out in which clean cotton swatches were immersed in a model wash liquor containing a fabric that released 0.1 g. of Direct Red 79 dye to solution. The amount of dye absorbed by the target fabric was determined by calculated $\Delta E$. The dye transfer inhibition performance was compared against polyvinyl pyrrolidone (PVP), a standard dye transfer inhibitor. In the data then, smaller scores are better.

| Dye Scavenging System | Delta E Signal |
|---|---|
| none | 8.6 |
| 18 ppm $H_2O_2$ | 10.5 |
| 21 ppm PVP | 4.2 |
| 18 ppm $H_2O_2$ + 1 ppm FeB | 2.4 |
| 18 ppm $H_2O_2$ + 1 ppm FeDCB | 2 |

The foregoing data demonstrate that not only do the inventive macrocyclic tetraamido compounds possess superior dye transfer inhibitory performance, but are measurably better than polyvinyl pyrrolidone, a known and effective DTI compound.

EXAMPLE 30

Dye transfer from Textile to Textile Using Acid Red 151

Experiments were performed according to Example 29 only using a release fabric that released 0.1 g of Acid Red 151.

| Dye Scavenging System | Delta E Signal |
|---|---|
| none | 26.3 |
| 18 ppm $H_2O_2$ | 32.6 |
| 21 ppm PVP | 30.7 |
| 18 ppm $H_2O_2$ + 1 ppm FeB | 2.5 |
| 18 ppm $H_2O_2$ + 1 ppm FeDCB | 2.8 |

In the next example, the performance of FeDCB on mustard and a naturally occurring clay soil were compared against a system containing $H_2O_2$ only. The performance on mustard, which is a cationically charged stain, demonstrates the stain specific superior performance of the inventive compounds.

EXAMPLE 31

Stain Removal of Mustard and Soil

This example demonstrates stain removal under simulated household laundry wash conditions. Fabrics stained with mustard or naturally occurring clay soil were washed with 2 g of All® liquid laundry detergent and an oxidant system (either $H_2O_2$ or $H_2O_2$ and the inventive catalyst FeDCB). Wash conditions were medium water level in warm water, cold water rinse, using a Terg-O-Tometer. Stain removal was measured and calculated using % soil removal (%SRE).

Thus, higher scores are preferred.

| Oxidant System | Mustard | Clay Soil |
|---|---|---|
| 18 ppm $H_2O_2$ | 63.6 | 56.3 |
| 18 ppm $H_2O_2$ + 0.5 ppm FeDCB | 71.5 | 59.8 |

In the next example, the anti-redeposition performance of the inventive compounds was compared against a control (no activator compound) and a commercially available organic bleach activator, tetraacetylethylenediamine (TAED).

EXAMPLE 32

Anti-Redeposition Comparison Study

| Anti-Redeposition Comparison Study | |
|---|---|
| System | Redeposition |
| Control | 0 |
| Control & FeDCB | 1.3 |
| Control & TAED | 0.7 |

The redeposition of soil is a measurement of the fabric using the Stensby Whiteness Calculation following the washing process. This study indicates that stray dyes are being destroyed in the aqueous wash liquor, preventing redeposition on fabrics; and that the invention's performance is superior versus TAED, a commercially available activator.

We claim:

1. A bleaching composition comprising:
   (a) an oxidatively stable bleach activator having the structure

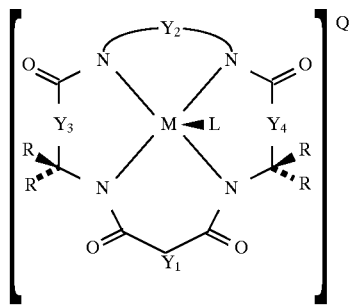

wherein $Y_1$, $Y_3$, and $Y_4$ each represent a bridging group, having zero, one, two or three carbon containing nodes for substitution, and $Y_2$ is a bridging group having at least one carbon containing node for substitution, each said node containing a C(R), C($R_1$)($R_2$), or a C(R)$_2$ unit and each R substituent is the same or different from the remaining R substituents and is selected from the group consisting of methyl, cycloalkyl, cycloalkenyl, alkenyl, aryl, alkynyl, alkylaryl, halogen, alkoxy, phenoxy, $CH_2CF_3$, $CF_3$ and combinations thereof, or form a substituted or unsubstituted benzene ring of which two carbon atoms in the ring form nodes in the Y unit, or together with a paired R substituent bound to the same carbon atom form a cycloalkyl or cycloalkenyl ring, which may include an atom other than carbon; M is a transition metal with oxidation states of I, II, III, IV, V or VI, or selected from the Groups 3 4. 5. 6, 7, 8, 9, 10, 11 and 12 of the Periodic Table; Q is any counterion which would balance the charge of the compound on a stoichiometric basis; and (b) an amount of a source of an oxidizing compound effective for bleaching.

2. The bleaching composition of claim 1 wherein said oxidizing compound is selected from the group consisting of hydrogen peroxide, hydrogen peroxide adducts, compounds capable of producing hydrogen peroxide in aqueous solution, organic peroxides, persulfates, perphosphates, and persilicates.

3. The bleaching composition of claim 1 further comprising a further adjunct selected from the group consisting of surfactants, fillers, builders, sequestrants, anti-oxidants, enzymes, fluorescent whitening agents, dyes, colorants, pigments, and other standard cleaning and/or laundering adjuncts.

4. The bleaching composition recited in claim 1 further comprising a ligand L bound to the transition metal M of the bleach activator.

5. The bleaching composition of claim 1 wherein the oxidatively stable bleach activator is a macrocyclic tetraamido ligand having the structure:

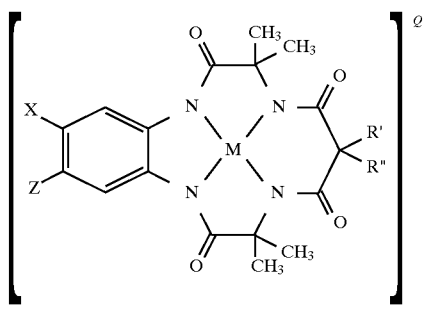

wherein X and Z may be H, electron donating or electron-withdrawing groups and R' and R" may be any combination of H, methyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon.

6. The bleaching composition of claim 5 wherein X and Z are independently selected from the group consisting of H, halogen, $SO_3^-$, $OSO_3^-$, $OSO_3$R (wherein R is H, alkyl, aryl, or alkylaryl) and $NO_2^-$.

7. The bleaching composition of claim 5 where R' and R" are selected from H and methyl, or combine to form a cyclobutyl, cyclopentyl or a cyclohexyl ring.

8. The bleaching composition of claim 5 wherein M is Fe or Mn.

9. The bleaching composition of claim 5 where R' and R" join together to form a cycloalkyl or cycloalkenyl, optionally with at least one atom which is not carbon.

10. The bleaching composition of claim 5 wherein X and Z are H.

* * * * *

UNITED STATES PATENT AND TRADEMARK OFFICE
CERTIFICATE OF CORRECTION

PATENT NO. : 5,876,625
DATED : March 2, 1999
INVENTOR(S) : Collins et al.

It is certified that error appears in the above-identified patent and that said Letters Patent is hereby corrected as shown below:

Title page,
In the figure, delete "0.4 mM [Fe(H$_2$O)DCB*]" and substitute therefor -- 0.4 $\mu$M [Fe(H$_2$O)DCB*]$^-$ --; therefor.
In the figure, delete "0.4 mM [Fe(H$_2$O)DCB" and substitute therefor -- 0.4 $\mu$M [Fe(H$_2$O)DCB]$^-$ --;
In the figure, delete "0.0 mM catalyst" and substitute therefor -- 0.0 $\mu$M catalyst --;
In the figure, delete "pH ~ 9 NaHCO$_3$/Na$_2$CO$_3$" and substitute therefor -- pH = 10 NaHCO$_3$/Na$_2$CO$_3$ --;
In the drawings, figure 3, delete "0.4 mM [Fe(H$_2$O)DCB*]-" and substitute therefor -- 0.4 $\mu$M [Fe(H$_2$O)DCB*]$^-$ --;
In the drawings, figure 3, delete "0.4 mM [Fe(H$_2$O)DCB]-" and substitute therefor -- 0.4 $\mu$M [Fe(H$_2$O)DCB]$^-$ --;
In the drawings, figure 3, delete "0.0 mM catalyst" and substitute therefor -- 0.0 $\mu$M catalyst --; and
In the drawings, figure 3, delete "pH ~ 9 NaHCO$_3$/Na$_2$CO$_3$" and substitute therefor -- pH = 10 NaHCO$_3$/Na$_2$CO$_3$ --.

Column 1,
Line 24, delete "nitrites" and substitute therefor -- nitriles --

Column 3,
Between lines 53 and 54, insert -- FIG. 4 depicts an iron (III) aqua complex reacting with hydroperoxide to give a purported oxo complex which it has been shown to exhibit catalytic properties for the oxidation of nitriles containing C-H bonds *alpha* to the cyano group. Fig. 5 depicts a structure wherein the oxo group and methylene H are restricted from as close an approach as in the ethyl case because the methylene group of the cyclopentyl substitutent cannot rotate freely to bring the two groups into as close a juxtaposition. --

Column 6,
Line 57, delete "nitrites" and substitute therefor -- nitriles --
Line 58, delete "a" and substitute therefor -- α --

Column 7,
Line 1, delete "K" and substitute therefor -- IR, --

Column 12,
Line 37, delete "nitrites" and substitute therefor -- nitriles --

UNITED STATES PATENT AND TRADEMARK OFFICE
CERTIFICATE OF CORRECTION

PATENT NO.   : 5,876,625
DATED        : March 2, 1999
INVENTOR(S)  : Collins et al.

It is certified that error appears in the above-identified patent and that said Letters Patent is hereby corrected as shown below:

Column 15,
Line 1, delete "finnel" and substitute therefor -- funnel --

Column 16,
Line 10, delete "$C_{,3}$" and substitute therefor -- $C_{13}$ --

Column 17,
Line 20, delete "$C_{21}H_{32}N_2O$." and substitute therefor -- $C_{21}H_{32}N_2O_3$ --
Line 48, delete "PCd," and substitute therefor -- $PCl_3$ --

Column 18,
Line 27, delete "PCI," and substitute therefor -- $PCl_3$ --
Line 45, delete "PC1," and substitute therefor -- $PCl_3$ --
Line 55, delete "$C_{21}H_{,o}N_4O_4$:" and substitute therefor -- $C_{21}H_{30}N_4O_4$ --

Column 19,
Line 60, delete "$C1_9H_{24}N_4O_4Cl_2$" and substitute therefor -- $C_{19}H_{24}N_4O_4Cl_2$ --

Column 20,
Line 36, delete "CDC1 and substitute therefor -- $CDCl_3$ --

Column 21,
Line 17, delete "$C_{21}H_{30}N_2O_4$" and substitute therefor -- $C_{22}H_{30}N_2O_4$ --.
Line 50, delete "[LN]2 and [$Et_4$ N]3" and substitute therefor -- [$Et_1$ N]2 and [$Et_1$ N]3 --.

Column 22,
Line 50, delete "$C_{46}H_{44}N,FeOCl_2P$:" and substitute therefor -- $C_{46}H_{44}N_5FeOCl_2P$: --.

Column 23,
Line 27, delete "[P?P]" and substitute therefor -- [$Ph_4P$] --
Line 56, delete "$F^{o2}$" (first occurrence) and substitute therefor -- $F_o^2$ --
Line 66, delete "$d_{calc}$" and substitute therefor -- $d_{calcd}$ --

UNITED STATES PATENT AND TRADEMARK OFFICE
CERTIFICATE OF CORRECTION

PATENT NO. : 5,876,625
DATED : March 2, 1999
INVENTOR(S) : Collins et al.

It is certified that error appears in the above-identified patent and that said Letters Patent is hereby corrected as shown below:

Column 24,
Line 30, delete "9" and substitute therefor -- 10 --;

Signed and Sealed this

Eighth Day of February, 2005

JON W. DUDAS
*Director of the United States Patent and Trademark Office*